US006245884B1

(12) United States Patent
Hook

(10) Patent No.: US 6,245,884 B1
(45) Date of Patent: Jun. 12, 2001

(54) SECRETASES RELATED TO ALZHEIMER'S DEMENTIA

(76) Inventor: Vivian Y. H. Hook, 8276 Caminito Maritimo, La Jolla, CA (US) 92037

( * ) Notice: Subject to any disclaimer, the term of this patent is extended or adjusted under 35 U.S.C. 154(b) by 0 days.

(21) Appl. No.: 09/173,887

(22) Filed: Oct. 16, 1998

(51) Int. Cl.[7] .......................... A61K 38/00; A61K 38/03; C07K 14/435

(52) U.S. Cl. .......................... 530/300; 424/9.2; 435/7.1; 435/23; 435/29; 435/69.2; 435/332; 435/326; 435/331; 514/18; 514/19; 514/299; 530/331; 530/350; 562/545; 562/577

(58) Field of Search ............................ 424/9.2; 435/7.1, 435/23, 29, 69.2, 332, 326, 331; 514/18, 19, 299; 530/331, 350, 300; 562/545, 577

(56) References Cited

U.S. PATENT DOCUMENTS

| 5,200,339 | 4/1993 | Abraham .............................. 435/212 |
| 5,604,102 | 2/1997 | McConlogue et al. ............... 435/7.1 |
| 5,703,129 | 12/1997 | Felsenstein et al. ................. 514/613 |
| 5,733,768 | 3/1998 | Dixon et al. .......................... 530/350 |
| 5,744,346 | 4/1998 | Chrysler et al. ..................... 435/226 |
| 5,891,887 | * 4/1999 | Markwell et al. ................... 514/299 |
| 5,942,400 | 8/1999 | Anderson et al. .................... 435/7.1 |

FOREIGN PATENT DOCUMENTS

| 92/00768 | 1/1992 | (WO) . |
| 96/40885 | 12/1996 | (WO) . |
| 98/03642 | 1/1998 | (WO) . |
| 98/13488 | 4/1998 | (WO) . |
| 98/15828 | 4/1998 | (WO) . |
| 98/21589 | 5/1998 | (WO) . |
| 98/26059 | 6/1998 | (WO) . |

OTHER PUBLICATIONS

Matsumoto et al., "The 68 kDa human beta–secretase in brains of Alzheimer's disease patients contains heparan sulfate glycoconjugate," *Neurobiol. of Aging*, 17 (4 supp.):S107 Abstract (1996).

Matsumoto et al, "Human brain beta–secretase contains heparan sulfate glycoconjugates," *Neurosci. Lett.*, 211:105–108 (1996).

Berg et al., "Composition of white matter bovine brain coated vesicles: evidence that several components influence β–amyloid peptide to form oligomers and aggregates in vitro," *Brain Res.* 752:72–80 (1997).

Campbell et al., "Identification of a protein kinase as an intrinsic component of rat liver coated vesicles," *Biochem.* 23:4420–4426 (1984).

Knops et al., "Evidence for a nonsecretory, acidic degradation pathway for amyloid precursor protein in 293 cells," *J. Biol. Chem.* 267(23):16022–16024 (1992).

Marks et al., "Hydrolysis of amyloid precursor protein–derived peptides by cysteine proteinases and extracts of rat brain clathrin–coated vesicles," *Peptides* 15(1):175–182 (1994).

Marks et al., "Brain cathepsin B but not metalloendopeptidases degrade rAPP[751] with production of amyloidogenic fragments," *Int. J. of Peptide & Protein Res.* 46:306–313 (1995).

Sambamurti et al., "Evidence for intracellular cleavage of the alzheimer's amyloid precursor in PC12 cells," *J. Neuroscience Res.* 33:319–329 (1992) 1.

Xia et al., "Presenilin 1 regulates the processing of β–amyloid precursor protein c–terminal fragments and the generation of amyloid β–protein in endoplasmic reticulum and golgi," *Biochem.* 37:16465–16471 (1998).

Abraham, C. et al., "Immunochemical Identification of the Serine Protease Inhibitor $\alpha_1$–Antichymotrypsin in the Brain Amyloid Deposits of Alzheimer's Disease," *Cell*, 52:487–501 (1988).

Abraham, C. et al., "Facile and Sensitive Assay for Monitoring Proteolytic Activities with Defined Specificities: Studies on Amyloid β–Protein Processing in Alzheimer's Disease," *Peptide Res.*, 3(5):211–215 (1990).

Azaryan, A. et al., "Characteristics of the Chromaffin Granule Aspartic Proteinase Involved in Proenkephalin Processing," *J. of Neurochem.*, 65(4):1771–1779 (1995).

Azaryan, A. et al., "Chromaffin Granule Aspartic Proteinase Processes Recombinant Proopiomelanocortin (POMC)," *Biochem. Biophys. Res. Commun.*, 215(3):937–944 (1995).

Azaryan, A. et al., "Distinct Properties of Prohormone Thiol Protease (PTP) Compared to Cathepsins B, L, and H: Evidence for PTP as a Novel Cysteine Protease," *Arch. Biochem. Biophys.*, 314(1):171–177 (1994).

Azaryan, A. et al., "Kex2–like Proteolytic Activity in Adrenal Medullary Chromaffin Granules," *Biochem. Biophys. Res. Commun.*, 185(1):398–403 (1992).

Azaryan, A. et al., "Purification and Characteristics of the Candidate Prohormone Processing Proteases PC2 and PC1/3 from Bovine Adrenal Medulla Chromaffin Granules," *J. Biol. Chem.*, 270:8201–8208 (1995).

Azaryan, A. et al., "Unique Cleavage Specificity of 'Prohormone thiol Protease' Related to Proenkephalin Processing," *FEBS Lett.*, 341:197–202 (1994).

Backstrom, J. et al., "Matrix Metalloproteinase–9 (MMP–9) Is Synthesized in Neurons of the Human Hippocampus and Is Capable of Degrading the Amyloid–β Peptide (1–40)," *J. Of Neuroscience*, 16(24):7910–7919 (1996).

(List continued on next page.)

Primary Examiner—Karen Cochrane Carlson
Assistant Examiner—Stephen Tu
(74) *Attorney, Agent, or Firm*—Campbell & Flores LLP

(57) ABSTRACT

This invention provides a method of determining the proteolytic activity of the in vivo secretases, particularly the β–secretase and γ–secretase that produce the Aβ peptides found in the plaques of Alzheimer Dementia (AD) patients. The invention also provides methods of isolating such secretases and methods of selecting agents that affect the activity of such secretases for developing drugs to treat or prevent dementia.

8 Claims, 5 Drawing Sheets

OTHER PUBLICATIONS

Bodovitz, S. et al., "Cholesterol Modulates α–Secretase Cleavage of Amyloid Precursor Protein," *J. Of Biological Chem.*, 271(8):4436–4440 (1996).

Brown, A. et al., "Evaluation of Cathepsins D and G and EC 3.4.24.15 as Candidate β–Secretase Proteases Using Peptide and Amyloid Precursor Protein Substrates," *J. Of Neurochem.*, 66(6):2436–2445 (1996).

Cataldo, A. et al., "Increased Neuronal Endocytosis and Protease Delivery to Early Endosomes in Sporadic Alzheimer's Disease: Neuropathologic Evidence for a Mechanism of Increased β–Amyloidogenesis," *J. Of Neurosci.*, 17(16):6142–6151 (1997).

Chang, T. et al., "A Novel Brain Cysteine Protease Forms and SDS Stable Complex with the β–Amyloid Precursor Protein$^α$," *Ann NY Acad. Sci.*, 777:183–188 (1996).

Chesselet, M. et al., "Carboxypeptidase H–like Immunoreactivity in the Striatum of Cats and Monkeys," *Regulatory Peptides*, 20:151–159 (1988).

Chevallier, N. et al., "Cathepsin D displays in vitro β–secretase–like specificity," *Brain Research*, 750:11–19 (1997).

Citron, M. et al., "Evidence that the 42–and 40–amino acid forms of amyloid β protein are generated from the β–amyloid precursor protein by different protease activities," *Proc. Natl. Acad. Sci. USA.*, 93:13170–13175 (1996).

Citron, M. et al., "Generation of Amyloid β protein from Its Precursor Is Sequence Specific," *Neuron.*, 14:661–670 (1995).

Citron, M. et al., "Inhibition of Amyloid β–Protein Production in Neural Cells by the Serine Protease Inhibitor AEBSF," *Neuron*, 17:171–179 (1996).

Cook, D. et al., "Alzheimer's Aβ(1–42) is generated in the endoplasmic reticulum/intermediate comparment of NT2N cells," *Nature Medicine*, 3(9):102–104 (1997).

Desdouits, F. et al., "Amyloid β Peptide Formation in Cell–Free Preparations," *J. Of Biological Chemistry*, 271(40):24670–24674 (1996).

Dugan, J. et al., "The Ras–related GTP–binding Protein, Rab1B, Regulates Early Steps in Exocytic Transport and Processing of β–Amyloid Precursor Protein," *J. Of Biological Chem.*, 270(18):10982–10989 (1995).

Efthimiopoulos, S. et al., "Cholinergic Agonists Stimulate Secretion of Soluble Full–length Amyloid Precursor Protein in Neuroendocrine Cells," *Proc. Natl. Acad. Sci. USA*, 93:8046–8050 (1996).

Efthimiopoulos, S. et al., "Intracellular Cyclic AMP Inhibits Constitutive and Phorbol Ester–Stimulated Secretory Cleavage of Amyloid precursor Protein," *J. Of Neurochem.*, 67(2):872–875 (1996).

Efthimiopoulos, S. et al., "Localization of Presenilin 1 Peptides in Neuronal Large Dense Core and Somatodendritic Clathin Coated Vesicles," *J. Neurochem.*, 71(6):2365–2372 (1998).

Evin, G. et al., "Candidate γ–Secretases in the Generation of the Carboxyl Terminus of the Alzheimer's Disease βA4 Amyloid: Possible Involvement of Cathepsin D," *Biochemistry*, 34:14185–14192 (1995).

Flagmeyer, I. et al., "General Pharmacology of the Putative Cognition Enhancer Linopirdine," *Arzneim.–Forsch./Drug Res.*, 45(1):456–459 (1995).

Games, D. et al., "Alzhemier–type neuropathology in transgenic mice overexpressing V717F β–amyloid precursor protein," *Nature*, 373:523–527 (1995).

Ghanta, J. et al., "A Strategy for Designing Inhibitors of β–Amyloid Toxicity," *J. Of Biol. Chem.*, 271(47):29525–29528 (1996).

Haass, C. et al., "The Swedish Mutation Causes Early–onset Alzheimer's Disease by B–secretase Cleavage Within the Secretory Pathway," *Nature Medicine*, 1(12):1291–1296 (1995).

Hartmann, T. et al., "Distinct Sites of Intracellular Production for Alzheimer's Disease Aβ40/42 Amyloid Peptides," *Nature Medicine*, 3(9):1016–1020 (1997).

Heisler, S. et al., "Corticotropin Releasing Factor Stimulation of Protein Carboxlmethylation in Mouse Pituitary Tumor Cells," *Biochem. Pharm.*, 32:1295–1299, (1983).

Heisler, S. et al., "Somatostatin Inhibits Multireceptor Stimulation of cyclic AMP Formation and Corticotropin Secretion in Mouse Pituitary Tumor Cells," *Proc. Natl. Acad. Sci. USA*, 79:6502–6506, (1982).

Higaki, J. et al., "Processing of β–Amyloid Precursor Protein by Cathepsin D," *J. Of Biol. Chem.*, 271(50):31885–31893 (1996).

Hines, V. et al., "The Expression And Processing Of Human β–Amyloid Peptide Precursors In *Saccharomyces Cerevisiae*: Evience For A Novel Endopeptidase In The Yeast Secretory System," *Cell. And Mole. Biol. Res.*, 40(4):273–284 (1994).

Ho, L. et al., "The Alternatively Spliced Kunitz Protease Inhibitor Domain Alters Amyloid β Protein Precursor Processing and Amyloid β Protein production in Cultured Cells," *J. Of Biol. Chem.*, 271(48):30929–30934 (1996).

Hook, V. et al., "Partial Purification of Nuclear Protein Kinase from Small Dense Nuclei of Mouse Brain and the Effect of Chronic Morphine Treatment," *J. Neurochem.*, 34:1274–1279, (1980).

Hook, V. et al., "Possible Nuclear Protein Kinase Regulation of Homologous Ribonucleic Acid Polymerases from Small Dense Nuclei of Mouse Brain During Morphine Tolerance–Dependence: Involvement of Cyclic 3', 5'–Adenosine Monophosphate," *Biochem. Pharm.*, 30(16):2313–2318, (1981).

Hook, V. et al., "Evidence for Biochemical Adaptation in Morphine Tolerance Dependence," In: Way El, ed. *Endogenous and Exogenous Opiate Agonists and Antagonist*, New York: Pergamon Press., pp.493–496.

Hook, V. et al., "A Carboxypeptidase Processing Enzyme for Enkephalin Precursors," *Nature*, 295:341–342, (1982).

Hook, V. et al., "Corticotropin Releasing Factor Stimulates Adrenocorticotropin and B–endorphin Release from Att–20 Mouse Pituitary Tumor Cells," *Biochem. Biophys. Res. Commun.*, 106(4):1364–1371, (1982).

Hook, V. et al., "Corticotropin–releasing Factor Stimulates Phospholipid Methylation and Corticotropin Secretion in Mouse Pituitary Tumor Cells," *Proc. Natl. Acad. Sci. USA.*, 79:6220–6224, (1982).

Hook, V. et al., "Carboxypeptidase B–like Converting Enzyme Activity in Secretory Granules of Rat Pituitary," *Proc. Natl. Acad. Sci. USA*, 81:2776–2780, (1984).

Hook, V. et al., "Carboxypeptidase B–like Activity for the Processing of Enkephalin Precursors in the Membrane Component of Bovine Adrenomedullary Chromaffin Granules," *Neuropeptides*, 4:117–126, (1984).

Hook, V. et al., "Two Peptidases That Convert $^{125}$i–lys–arg–[Met]enkephalin and $^{125}$i–[Met]enkephalin–arg$^6$, Respectively, to $^{125}$i[met]enkephalin in Bovine Adrenal Medullary Chromaffin Granules," *FEBS Lett*, 72(2):212–218, (1984).

Hook, V. et al., "Immunochemical Characterization of Carboxypeptidase B–like Peptide Hormone–Processing Enzyme," *Proc. Natl. Acad. Sci. USA,* 82:4745–4749 (1985).

Hook, V. et al., "Selective Regulation of Carboxypeptidase Peptide Hormone Processing enzyme during Enkephalin Biosynthesis in Cultured Bovine Adrenomedullary Chromaffin Cells," *J. Biol. Chem.,* 260(10):5991–5997, (1985).

Hook, V. et al., "[Met]enkephalin and Carboxypeptidases Processing Enzyme Are Co–released from Chromaffin Cells by Cholinergic Stimulation," *Biochem. Biophys. Res. Commun.,* 128:563–570, (1985).

Hook, V. et al., "Differential Distribution of Caroxypeptidase Processing Enzyme Activity and Immunoreactivity in Memebrane and Soluble Components of Chromaffin Granules," *J. Neurochem.,* 45(3):987–989, (1985).

Hook, V. et al., "Modulation of Carboxypeptidase Processing Enzyme Activity," In: Moody TW, ed. 5th International Spring Symposium, *Neural and Endocrine Peptides and Receptors,* Pergamon Press, pp. 599–606, (1986).

Hook, V. et al., "Biosynthesis and Maturation of Carboxypeptidase H," *Ann. N.Y. Acad. Sci.,* 493:394–396, (1986).

Hook, V. et al., "Distribution of Enkephlin–Containing Peptides Within Bovine and Chromaffin Granules," *Neuropeptides,* 9:263–267, (1987).

Hook, V. et al., "Product Inhibition of Carboxypeptidase H," *J. Biol. Chem.,* 262(26):12583–12588, (1987).

Hook, V. et al., "Regulation of Carboxypeptidase H By Inhibitory and Stimulatory Mechanisms During Neuropeptide Precursor Processing," *Cell. Mol. Neurobiol.,* 8(1):49–55, (1988).

Hook, V. et al., "Differential Regulation of Carboxypeptidase H, a Peptide Precursor Processing Enzyme, and Catecholamines in Adrenal Medulla," In: Sandler M, ed., *Process in Catecholamine Research, Part A: Basic Aspects and Peripheral Mechanisms,* Alan R. Liss, Inc., pp.263–270, (1988).

Hook, V. et al., "Identification of Zymogen and Mature Forms of Human Carboxypeptidase H: A Processing Enzyme for the Synthesis of Peptide Hormones," *FEBS Lett,* 238(2):338–342, (1988).

Hook, V. et al., "Cleavage of Recominant Enkephalin Precursor By Endoproteolytic Activity in Bovine Chromaffin Granules," *Biochem. Biophys. Res. Commun.,* 167(2):722–730, (1990).

Hook, V. et al., "Arginine and Lysine Product Inhibition of Bovine Adrenomedullary Carboxypeptidase H, A Prohormone Processing Enzyme," *Life Sci.,* 47(2):1135–1139, (1990).

Hook, V. et al., "Carboxypeptidase H in the Hypothalamo-Neurohypophysial System: Evidence for Processing and Activation of a Prohormone–Processing Enzyme During Axonal Transport," *J. Neurosci.,* 10(10):3219–3226, (1990).

Hook, V. et al., "Biosynthesis of Endogenous Opiate Peptides by Proteolytic Precursor Processing Mechanisms," In: Watson R, ed., *Biochemistry and Physiology of Sbstance Abuse,* 3rd ed. Boca Raton: CRC Press, Inc., pp. 367–377, (1991).

Hook, V. et al., "Proteases for Neuropeptide Precursor Processing in Bovine Adrenal Medullary Chromaffin Granules," In: Moody TW, ed., *Growth Factors, Peptides and Receptors,* New York: Plenum Press, pp.61–70, (1993).

Hook, V.Y.H., "Role of a Protease Inhibitor, Antichymotrypsin in Prohormone Procesing," ICOP Newsletter, (1993).

Hook, V. et al., "Purification and Characterization of $\alpha_1$–Antichymotrypsin–like Protease Inhibitor that Regulates Prohormone Thiol Protease Involved in Enkephalin Precursor Processing," *J. Biol. Chem.,* 268(27):20570–20577, (1993).

Hook, V. et al., "Proteases and the Emerging Role of Protease Inhibiors in Prohormone Processing," *FASEB J.,* 8:1269–1278, (1994).

Hook, V. et al., "The Processing Proteases Prohormone Thiol Protease, PC1/3 and PC2, and 70–kDa Aspartic Proteinase Show Preferences among Proenkephalin, Pro-neuropeptide Y, and Proopiomelanocortin Substrates," *Arch. Biochem. Biophysics.,* 328(1):107–114, (1996).

Hook, V. et al., "Proenkephalin–processing Enzymes in Chromaffin Granules: A Model for Neuropeptide Biosynthesis," *Ann. N.Y. Acad. Sci.,* 780:121–133, (1996).

Hook, V. et al., "Production of Radiolabeled Neuropeptide Precursors by in vitro Transcription and Translation," *Peptide Research,* 9(4):183–187, (1996).

Hook, V. et al., "High–level Expression of the Prohormones Proendephalin, Pro–neuropeptide Y, Proopiomelanocortin, and $\beta$–Protachykinin for In Vitro Prohormone Processing," *Protein Expression Purif.,* 10:80–88, (1997).

Hook, V.Y.H., "Prohormone Processing and $\alpha_1$–antichymotrypsin as a Potential Endognous Inhibitor," In: Macready N, ed., *Protease Inhibitors, Novel Therapeutic Application and Development,* Southborough, MA: IBC Library Series pp.6.2.1–6.2.22., (1997).

Hook, V.Y.H., "Prohormone Thiol Protease (PTP)," In: Barrett AJ, ed., *Handbook of Proteolytic Enzymes,* Academic Press pp.779–782, (1998).

Hook, V. et al., "'Prohormone Thiol Protease' (PTP), a novel Cysteine Protease for Proenkephalin and Prohormone Processing," In: Hook, V.Y.H., ed., *Proteolytic and Cellular Mechanisms in Prohormone and Proprotein Processing,* Austin, TX: R.G. Landes, Co. pp.89–104, (1998).

Hook, V. et al., "Carboxypeptidase and Aminopeptidase Proteases in Pro–neuropeptide Processing," In: Hook, V.Y.H., ed., *Proteolytic and Cellular Mechanisms in Prohormone and Proprotein Processing,* Austin, TX: R.G. Landes Co. pp.121–139, (1998).

Howland, D. et al., "Mutant and Native Human $\beta$–Amyloid Precursor Proteins in Transgenic Mouse Brain," *Neurobiology of Aging,* 16(4):685–699 (1995).

Hwang, S. et al., "Identification of Carboxypeptidase H Transcripts by Antisense RNA," *Mol. Brain Res.,* 25:135–139, (1994).

Hwang, S. et al., "Molecular Cloning Reveals Isoforms of Bovine $\alpha_1$–antichymotrypsin," *Proc. Natl. Acad. Sci. USA,* 91:9579–9583, (1994).

Hwang, S. et al., "Molecular Cloning of an Isoform of Phenol Sulforansforase from Human Brain Hippocampus," *Biochem. Biophys. Res. Commun.,* 207(2):701–707, (1995).

Hwang, S. et al., "Unique Reactive site Domains of Neuroendocrine Isoforms of Alpha$_1$–Antichymotrypsin from Bovine Adrenal Medulla and Pituitary Revealed by Molecular Cloning," *FEBS Lett,* 368:471–476, (1995).

Hwang, S. et al., "High Level Expression and Characterization of Recombinant Human Hippocampus Phenol Sulfotransferase: A Novel Phenol–Sulfating Form of Phenol Sulfotransferase," *Protein Expression Purif.,* 11:125–134, (1997).

Hwang, S. et al., "Neuroendocrine α₁–antichymotypsin as a possible Regulator of Prohormone and Neuropeptide Precursor Processing," In: Hook, V.Y.H., ed., *Proteolytic and Cellular Mechanisms in Prohormone and Proprotein Processing*, Austin, TX:R.G. Landes, pp.159–171, (1998).

Ida, N. et al., "Rapid Cellular Uptake of Alzheimer Amyloid Ba4 Peptide by Cultured Human Neuroblastoma Cells," *FEBS Letters*, 394:174–178 (1996).

Johnson–Wood, K. et al., "Amyloid Precursor Protein Processing and Aβ₄₂ Deposition in a Transgenic Mouse Model of Alzheimer Disease," *Proc. Natl. Acad. Sci. USA*, 94:1550–1555, (1997).

Kelly, J. et al., "Amyloid B–peptide Disrupts Carbchol–induced Muscarinic Cholinergic Signal Transduction in Coritcal Neurons," *Proc. Natl. Acad. Sci. USA*, 93:6753–6758 (1996).

Klafki, H.W. et al., "The Carboxyl Termini of β–Amyloid Peptides 1–40 and 1–42 Are Generated by Distinct γ–Secretase Activities," *J. Biol. Chem.*, 271(45):28655–28659 (1996).

Kounnas, M. et al., "LDL Receptor–Related Protein, a Multifunctional ApoE Receptor, Binds Secreted β–Amyloid Precursor Protein and Mediates Its Degradation," *Cell.*, 82:331–340 (1995).

Kreiger, T. et al., "Purification and Characterization of a Novel Thiol Protease Involved in Processing the Enkephalin Precursor," *J. Biol. Chem.*, 266(13):8376–8383, (1991).

Krieger, T. et al., "Prohormone Thiol Protease and Enkephalin Precursor Processing: Cleavage at Dibasic and Monobasic Sites," *J. Neurochem*, 59(1):26–31, (1992).

Krieger, T.et al., "Purification and Characterization of a Cathepsin D Protease from Bovine Chromaffin Granules," *Biochem.*, 31:4223–4231, (1992).

Laslop, A. et al., "Identification of Two Glycoproteins of Chromaffin Granules as the Carboxypeptidase H," *Neurosci. Lett*, 72:300–304, (1986).

LeBlanc, A. et al., "Processing of Amyloid Precursor Protein in Human Primary Neuron and Astrocyte Cultures," *J. Of Neurochem.*, 68(3):1183–1190, (1997).

Lee, R. et a l., "Metabotropic Glutamate Receptors Increase Amyloid Precursor Protein Processing in Astrocytes: Inhibition by Cyclic AMP," *J. Of Neurochem.*, 68(5):1830–1835 (1997).

Lemere, C. et al., "The E280a Presenilin 1 Alzheimer Mutation Produces Increased Aβ42 Deposition and Severe Cerebellar Pathology," *Nature Medicine*, 2(10):1146–1150, (1996).

Li, Q. et al., "Proteolytic Processing of Alzheimer's Disease βA4 Amyloid Precursor Protein in Human Platelets," *The American Soc. For Biochem. And Molecular Biology Inc.*, 270(23):14140–14147, (1995).

Lieb, K. et al., "Interleukin–1β and Tumor Necrosis Factor–α Induce Expression of α₁–Antichymotrypsin in Human Astrocytoma Cells by Activation of Nuclear Factor–κB," *J. Of Neurochem.*, 67(5:2039–2044 (1996).

Little, S. et al., "Zyme, a Novel and Potentially Amyloidogenic Enzyme cDNA Isolated from Alzheimer's Disease Brain," *J. Of Biological Chemistry*, 272(40):25135–25142, (1997).

Marx, J., "Dissecting How Presenilins Function–and Malfunction," *Science*, 274:1838–1840, (1996).

Meckelein, B. et al., "Human Endopeptidase (THOP1) Is Localized on Chromosome 19 Within the Linkage Region for the Late–Onset Alzheimer Disease AD2 Locus," *Genomics*, 31:246–249 (1996).

Moechars, D. et al., "Expression in Brain of Amyloid Precursor Protein Mutated in the A–secretase Site Causes Disturbed Behavior, Neuronal Degeneration and Premature Death in Transgenic Mice," *EMBO Journal*, 15(6):1265–1274 (1996).

Mok,S. et al., "A Novel Metalloprotease in Rat Brain Cleaves the Amyloid Precursor Protein of Alzheimer's Disease Generating Amyloidogenic Fragments," *Biochemistry*, 36(1):156–163, (1997).

Nelson, R. et al., "Clipsin, a Chymotrypsin–like Protease in Rat Brain Which Is Irreversibly Inhibited by α–1–Antichymotrypsin," *J. Of Biol. Chem.*, 265(7):3836–3843 (1990).

Nelson, R. et al., "Identification of a Chymotrypsin–like Mast Cell Protease in Rat Brain Capable of Generating the N–terminus of the Alzheimer Amyloid B–protein," *J. Of Neurochem.*, 61(2):567–577, (1993).

Papastoitsis, G. et al., "Identification of a Metalloprotease from Alzheimer's Disease Brain Able to Degrade the B–Amyloid Precursor Protein and Generate Amyloidogenic Fragments," *Biochemistry*, 33(1):192–199, (1994).

Perez, R. et al., "Enhanced Release of Amyloid β–Protein from Condon 670/671 "Swedish" Mutant β–Amyloid Precursor Protein Occurs in Both Secretory and Endocytic Pathways," *J. Of Biol. Chem.*, 271(15):9100–9107 (1996).

Petryniak, M. et al., "Elevated Intracellular Calcium Concentration Increases Secretory Processing of the Amyloid Precursor Protein by a Tyrosine Phosphorylation–dependent Mechanism," *J. Biochem.*, 320:957–963 (1996).

Price, D. et al., "Amyloid Beta Amyloidosis in Alzheimer's Disease," *Current Opinion in Neurology*, 8:268–274 (1995).

Qui, W. et al., "Degradation of Amyloid B–protein by a Metalloprotease Secreted by Microglia and Other Neural and Non–neural Cells," *J. Of Biol. Chem.*, 272(10):6641–6646 (1997).

Racchi, M. et al., "Secretory Processing of Amyloid Precursor Protein is Inhibited by Increase in Cellular Cholesterol Content," *J. Biochem.*, 322:893–898 (1997).

Reaume, A. et al., "Enhanced Amyloidogenic Processing of the β–Amyloid Precursor Protein in Gene–targeted Mice Bearing the Swedish Familial Alzheimer's Disease Mutations and a Humanized Aβ Sequence," *J. Of Biol. Chem.*, 271(38):23380–23388 (1996).

Reisine, T. et al., "Multireceptor–induced Release of Adrenocorticotropin from Anterior Pituitary Tumor Cells," *Biochem. Biophys. Res. Commun.*, 108:1251–1257, (1982).

Reisine, T. et al., "Activation of $B_2$–adrenergic Receptors on Mouse Anterior Pituitary Tumor Cells Increase Cyclic Adenosine 3':5'–monophosatesynthesis and Adrenocorticortropin Release," *J. Neurosci.*, 3(4):725–732, (1984).

Robakis, N. et al., "Biological Function and Processing of App.," In: Iqbal K, Motimer JA, Winblad B, Wisniewski HM, eds., *Research advances in Alzheimer's Disease and Related Disorders*, John Wiley & Sons, Ltd. pp.685–692, (1995).

Rubin, H. et al., "Cloning, Expression, Purification, and Biological Activity of Recombinant Native and Variant Human α1–Antichymotrypsins," *The J. Of Biological Chemistry*, 265(2):1199–1207, (1990).

Saftig, P. et al., "Amyloidogenic Processing of Human Amyloid Precursor Protein in Hippocampal Neurons Devoid of Cathepsin D," *J. Of Biol. Chem.,* 271(44):27241–27244, (1996).

Schiller, M. et. al., "'Prohormone Thiol Protease' (Ptp) Processing of Recombinant Proenkephalin," *Biochem.,* 34:7988–7995, (1995).

Schiller, M. et al., "Expression of Recombinant Pro-neuropeptide Y, Proopiomelanocortin, and Proenkephalin: Relative Processing by 'Prohormone Thiol Protease' (PTP)," *FEBS Lett,* 382:6–10, (1996).

Schönlein, C. et al., "Purification And Characterization of A Novel metalloprotease From Human Brain With The Ability To Cleave Substrates Derived From The N–Terminus Of β–Amyloid Protein," *Biochem. Biophys. Res. Comm.,* 201(1):45–53, (1994).

Schubert, D., "Serpins Inhibit the Toxicity of Amyloid Peptides," *European Journal of Neuroscience,* 9:770–777, (1997).

Schwarzenbrunner, U. et al., "Sympathetic Axons and Nerve Terminals: the Protein Compositionof Small and Large Dense–core and of a Third Type of Vesicles," *Neurosci.,* 37(3):819–827, (1990).

Seubert, P. et al., "Secretion of B–amyloid Precursor Protein Cleaved at the Amino Terminus of the B–amyloid Peptide," *Nature,* 361:260–263, (1993).

Shinoda, M. et al., "Specific Inhibitor for Prolyl Endopeptidase Suppresses the Generation of Amyloid β Protein in NG108–15 Cells," *Biochem. Biophys. Res. Comm.,* 235(3):641–645, (1997).

Simons, M. et al., "Amyloidogenic Processing of the Human Amyloid Precursor Protein in Primary Cultures of Rat Hippocampal Neurons," *J. Of Neuroscience,* 16(3):899–908, (1996).

Sisodia, S. et al., "Role of the β–amyloid protein in Alzheimer's Disease," *FASEB Journal,* 9:366–370, (1995).

Stephens, D. et al., "Metabolites of the β–Amyloid Precursor Protein Generated by β–Secretase Localise to the Trans-–Golgi Network and Late Endosome in 293 Cells," *J. Of Neuroscience Res.,* 46:211–225, (1996).

Suzuki, T. et al., "Phosphorylation of Alzheimer β–Amyloid Precursor–like Proteins," *Biochemistry,* 36:4643–4649, (1997).

Tezapsidis, N. et al., "Stimulation of 'Prohormone Thiol Protease' (Ptp) and [Met]enkephalin for Forskolin: Blockade of Elevated [Met]enkephalin by Cysteine Protease Inhibitor of Ptp," *J. Biol. Chem.,* 270(22):13285–13290, (1995).

Tezapsidis, N. et al., "Release of Nontransmembrane Full-length Alzheimer's Amyloid Precursor Protein from the Lumenar Surface of Chromaffin Granule Membranes," *Biochem.,* 37:1274–1282, (1998).

Thinakaran, G. et al., "Metabolism of the "Swedish" Amyloid Precursor Protein Variant in Neuro2a (N2a) Cells," *J. Of Biol. Chem.,* 271(16):9390–9397, (1996).

Tischer, E. et al., "β–Amyloid Precursor Protein, Location of Transmembrane Domain and Specificity of $_r$–Secretase Cleavage," *J. Of Biol. Chem.,* 271(36):21914–21919, (1996).

Tjernberg, L. et al., "Generation of Alzheimer Amyloid β peptide through Nonspecific Proteolysis," *J. Of Biol. Chem.,* 272(3):1870–1875, (1997).

Toomin, C. et al., "Thiol and Aspartyl Proteolytic Activities in Secretory Vesicles of Bovine Pituitary," *Biochem. Biophys. Res. Commun.,* 18(2):449–455, (1992).

Toide, K. et al., "A Novel Prolyl Endopeptidase Inhibitor, Jtp–4819, with Potential for Treating Alzhemier's Disease," *Behavioural Brain Research,* 83:147–151, (1997).

Turner, R. et al., "Amyloids $β_{40}$ and $β_{42}$ Are Generated Intracellularly in Cultured Human Neurons and Their Secretion Increases with Maturation," *J. Of Biol. Chem.,* 272(15):8966–8970, (1996).

Vassilacopoulou, D. et al., "Full–length and Truncated Alzheimer Amyloid Precursors in Chromaffin Granules: Solubilization of Membrane Amyloid Precursor Is Mediated by an Enzymatic Mechanism," *J. Neurochem.,* 64:2140–2146, (1995).

Wang, R. et al., "The Profile of Soluble Amyloid β Protein in Cultured Cell Media," *J. Of Biol. Chem.,* 271(50):31894–31902, (1996).

Waters, S. et al., "Alterations of Peptide Metabolism and Neuropeptidase Activity in Senile Dementia of the Alzheimer's Type$^a$," *Ann NY Acad. Sci.,* 814:30–39, (1997).

Wolozin, B. et al., "Differential Expression of a Carboxyl Terminal Derivatives of Amyloid Precursor Protein Among Cell Lines," *J. Of Neurosci. Res.,* 33:163–169, (1992).

Yasothornsrikul, S. et al., "Arginine and Lysine Aminopeptidase Activities in Chromafin Granules of Bovine Adrenal Medulla: Relevance to Prohormone Processing," *J. Neurochem.,* 70:153–163, (1998).

Zhao, J. et al., "β–Secretase Processing of the β–Amyloid Precursor Protein in Transgenic Mice Is Efficient in Neurons but Inefficient in Astrocytes," *J. Of Biol. Chem.,* 271(49):31407–31411, (1996).

\* cited by examiner

Figure 2.

Endoprotease
clevage

1   #2   #3
         ↓    ↓    ↓
Z*Val-Lys-Met-MCA

SEQUENCE LISTING

```
<160> NUMBER OF SEQ ID NOS: 5

<210> SEQ ID NO: 1
<211> LENGTH: 4
<212> TYPE: PRT
<213> ORGANISM: mammalian

<400> SEQUENCE: 1

Val Lys Met Asp
  1

<210> SEQ ID NO: 2
<211> LENGTH: 4
<212> TYPE: PRT
<213> ORGANISM: mammalian

<400> SEQUENCE: 2

Gly Val Val Ile
  1
```

```
<210> SEQ ID NO: 3
<211> LENGTH: 4
<212> TYPE: PRT
<213> ORGANISM: mammalian

<400> SEQUENCE: 3

Val Ile Ala Thr
  1

<210> SEQ ID NO: 4
<211> LENGTH: 4
<212> TYPE: PRT
<213> ORGANISM: mammalian

<400> SEQUENCE: 4

Ile Ala Thr Val
  1

<210> SEQ ID NO: 5
<211> LENGTH: 53
<212> TYPE: PRT
<213> ORGANISM: mammalian

<400> SEQUENCE: 5

Val Lys Met Asp Ala Glu Phe Arg His Asp Ser Gly Tyr Glu Val His
  1               5                  10                  15

His Gln Lys Leu Val Phe Phe Ala Glu Asp Val Gly Ser Asn Lys Gly
             20                  25                  30

Ala Ile Ile Gly Leu Met Val Gly Gly Val Val Ile Ala Thr Val Ile
         35                  40                  45

Val Ile Thr Leu Val
     50
```

SECRETASES RELATED TO ALZHEIMER'S DEMENTIA

This invention was made with government support under grant number NS24553 awarded by the National Institutes of Neurological Disease and Stroke. The government has certain rights in the invention.

BACKGROUND OF THE INVENTION

1. Field of the Invention

The present invention relates generally to medicine. More specifically, the invention is directed to methods relating to treating or preventing dementia.

2. Background Information

Dementia is a neurological disease that results in loss of intellectual capacity and is associated with widespread reduction in the number of nerve cells and brain tissue shrinkage. Memory is the mental capacity most often affected. The memory loss may first manifest itself in simple absentmindedness, a tendency to forget or misplace things, or to repeat oneself in conversation. As the dementia progresses, the loss of memory broadens in scope until the patient can no longer remember basic social and survival skills and function independently. Dementia can also result in a decline in the patient's language skills, spatial or temporal orientation, judgment, or other cognitive capacities. Dementia tends to run an insidious and progressive course.

Dementia results from a wide variety of distinctive pathological processes. The most common pathological process to cause dementia is Alzheimer's disease, which results in Alzheimer's-type dementia (AD). The second most common cause is multi-infarct, or vascular dementia, which results from hypertension or other vascular conditions. Dementia can also result from infectious disease, such as in Creutzfeldt-Jakob disease. Dementia occurs in Huntington's disease, which is caused by an autosomal dominant gene mutation, and in Parkinson's disease, which is associated with a motor disorder. Dementia also occurs from head injury and tumors.

Rare before age 50, AD affects nearly half of all people past the age of 85, which is the most rapidly growing portion of the United States population. As such, the current 4 million AD patients in the United States are expected to increase to about 14 million by the middle of the next century.

No method of preventing AD is known and treatment is primarily supportive, such as that provided by a family member in attendance. Stimulated memory exercises on a regular basis have been shown to slow, but not stop, memory loss. A few drugs, such as tacrine, result in a modest temporary improvement of cognition but do not stop the progression of dementia.

A hallmark of AD is the accumulation in brain of extracellular insoluble deposits called amyloid plaques, and abnormal lesions within neuronal cells called neurofibrillary tangles. The presence of amyloid plaques, together with neurofibrillary tangles, are the basis for definitive pathological diagnosis of AD. Increased plaque formation is associated with increased risk of AD.

The major components of amyloid plaques are the amyloid β-peptides, also called Aβ peptides, which consist of three proteins having 40, 42 or 43 amino acids, designated as the $A\beta_{1-40}$, $A\beta_{1-42}$, and $A\beta_{1-43}$ peptides. The amino acid sequences of the Aβ peptides are known and the sequence of the $A\beta_{1-42}$ is identical to that of the $A\beta_{1-40}$ peptide, except that the $A\beta_{1-42}$ peptide contains two additional amino acids at its carboxyl (COOH) terminus. Similarly, the amino acid sequence of the $A\beta_{1-43}$ peptide is identical to that of the $A\beta_{1-42}$ peptide except that the $A\beta_{1-43}$ peptide contains one additional amino acid at its carboxyl terminus. The Aβ peptides are thought to cause the nerve cell destruction in AD, in part, because they are toxic to neurons in vitro and in vivo.

The Aβ peptides are derived from larger amyloid precursor proteins (APP proteins), which consist of four proteins, designated as the $APP_{695}$, $APP_{714}$, $APP_{751}$, and $APP_{771}$ proteins, which contain 695, 714, 751 or 771 amino acids, respectively. The different APP proteins result from alternative ribonucleic acid splicing of a single APP gene product. The amino acid sequences of the APP proteins are also known and each APP protein contains the amino acid sequences of the Aβ peptides.

Proteases are believed to produce the Aβ peptides by recognizing and cleaving specific amino acid sequences within the APP proteins at or near the ends of the Aβ peptides. Such sequence specific proteases are thought to exist because they are necessary to produce from the APP proteins the $A\beta_{1-40}$, $A\beta_{1-42}$, and $A\beta_{1-43}$ peptides consistently found in plaques.

But the proteases have not been isolated. Nonetheless, they have been named "secretases" because the Aβ peptides which they produce are secreted by cells into the extracellular environment. Moreover, the secretases have been named according to the cleavages that must occur to produce the Aβ peptides. The secretase that cleaves the amino terminal end of the Aβ peptides is called the β-secretase and that which cleaves the carboxyl terminal end of the Aβ peptides is called the γ-secretase. The γ-secretase determines whether the $A\beta_{1-40}$, $A\beta_{1-42}$, or $A\beta_{1-43}$ peptide is produced (see FIG. 1). But since the secretases have not been isolated, the terms β-secretase and γ-secretase each could relate to one or several protease species.

In addition to the Aβ peptides, proteolytic cleavage of another specific amino acid sequence within the APP proteins is known to occur and to produce α-APP and 10 kilodalton (kDa) fragments. That amino acid sequence lies within the Aβ peptide amino acid sequence of the APP proteins. Like the β-secretase and the γ-secretase, the protease responsible for that cleavage has also not been isolated but has been named the α-secretase (see FIG. 1). Significantly, the products produced by the (-secretase cleavage, the β-APP and the 10 kilodalton (kDa) fragments, do not form senile plaques.

Proteases can be isolated from tissue homogenates or lysed cell samples, but those samples can contain the proteases from cell organelles in which the product is not produced, but which may be able to cleave in vitro the precursor protein to produce the product. Thus, a problem in using such samples to isolate the secretases has been that proteases which produce the Aβ peptide in vitro, but not in vivo, may be erroneously isolated.

The problem can be avoided by isolating the secretase from cell organelles in which the APP proteins are processed in vivo. A cell organelle thought to be a site in which such processing occurs is the secretory vesicles of brain neuronal cells. But methods have not been developed to obtain sufficient amounts of pure secretory vesicles from neuronal cells to assay for secretase activity in those vesicles.

Large amounts of pure secretory vesicles can be obtained from chromaffin cells, neuroendocrine cells of the adrenal medulla, and have been used to obtain proteases. For example, carboxypeptidase H (CPH), prohormone thiol protease (PTP), and the prohormone convertases (PC1 and PC2), which process precursor proteins into peptides having opiate activity have been obtained from such vesicles. But chromaffin cells have not been shown to produce the Aβ peptides or have secretase activity.

The β-secretase, γ-secretase, and α-secretase must be isolated to understand how the neurotoxic Aβ peptides are produced so that AD can be prevented or treated. To isolate the secretase, new methods are needed for assaying the proteolytic activity of secretases in substantially purified preparations of the cell organelles in which the APP protein is processed in vivo. Moreover, new screening methods for selecting agents that affect the proteolytic activity of the secretases are needed to develop new pharmaceuticals for treating or preventing AD.

The invention satisfies these needs by providing new methods of determining the proteolytic activity of secretases and isolating secretases having that activity. The invention also provides new screening methods for selecting agents that affect the activity of such secretases.

SUMMARY OF THE INVENTION

The invention is directed to a method of determining the proteolytic activity of a secretase by obtaining substantially pure vesicles, permeablizing the vesicles and incubating the permeabilized vesicles with an APP substrate. The activity of the secretase is determined by detecting the cleavage of the APP substrate which is proportional to that activity. The invention is also directed to a method of isolating the secretase having that activity and the secretase obtained by that isolation method.

The invention is further directed to methods of selecting an agent that alters the cleavage of an APP substrate by a secretase. In one method, substantially pure vesicles are obtained, permeabilized, and incubated with an APP substrate with and without the agent. The cleavage of the APP substrate with and without the agent is compared and the agent that alters the cleavage of the APP substrate selected. In another method, an isolated secretase and an APP substrate are incubated with and without the agent, the cleavage of the APP substrate compared and the agent selected that alters the cleavage of the substrate. In yet another method, a cell is selected by determining whether the cells contains vesicles having the proteolytic activity of a secretase and those cells used to select an agent. The production of an APP protein or an APP derived product produced by those cells with and without the agent is compared and the agent is selected that alters the production of the product. Another aspect of the invention is the agent selected by such methods.

BRIEF DESCRIPTION OF THE DRAWINGS

FIG. 2. The bonds, labeled #1, #2, and #3, in the Z*Val-Lys-Met-MCA substrate cleaved by a secretase having endoprotease activity are shown. The Z, Val, Lys, Met, and MCA in the substrate represent a carbobenzoxy, valine, lysine, methionine, and aminomethylcourmarinamide group, respectively. The star (*) and dash (-) represent nonpeptide and peptide bonds, respectively FIG. 3. The fluorescence activity is plotted as a function of the pH at which a lysate of substantially pure chromaffin vesicles is incubated with the Z*Val-Lys-Met-MCA substrate. The fluorescence activity is the relative fluorescence of the free MCA (AMC) released by proteolytic cleavage of the substrate.

DETAILED DESCRIPTION OF THE INVENTION

Figure 1:
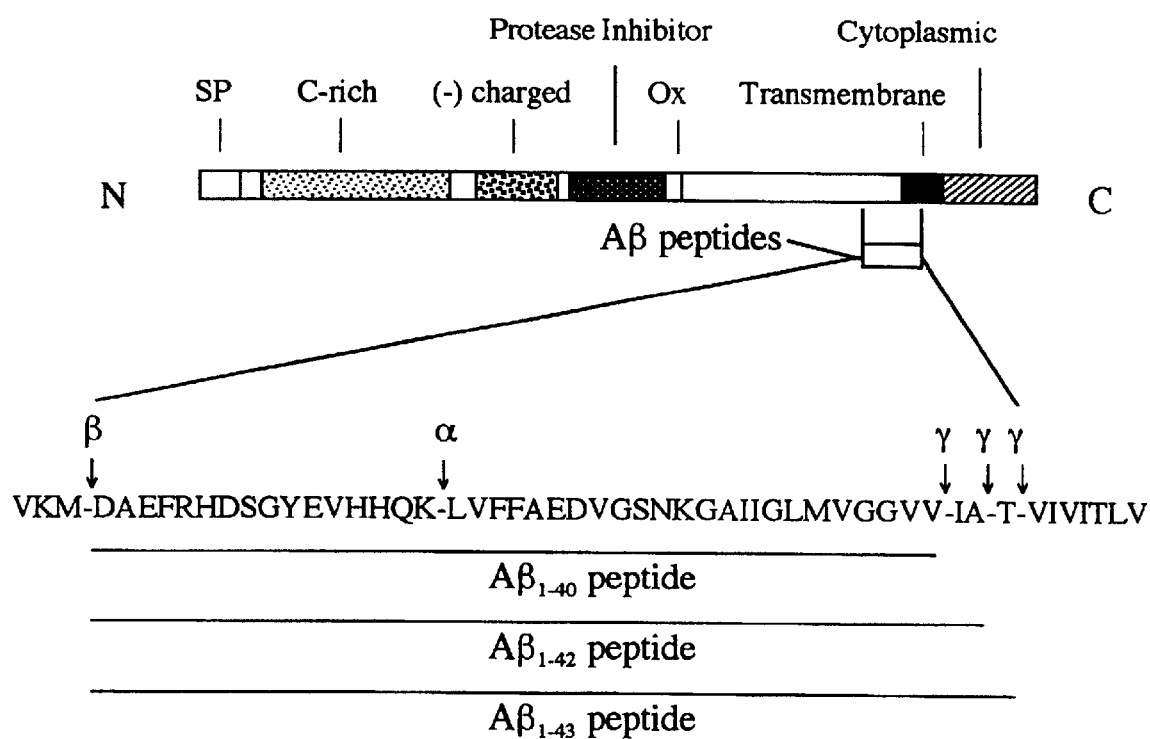
FIG. 1. The upper bar is a diagram of an amyloid precursor protein (APP protein). The amino and carboxyl termini of the APP protein are indicated by the letters "N" and "C," respectively. The relative location of various known regions within the APP protein are indicated, including the signal peptide (SP), cysteine-rich (C-rich), negatively charged ((−)charged), -protease inhibitor, Ox antigen (Ox), transmembrane, cytoplasmic and Aβ peptide regions. The amino acid sequence of the Aβ peptides and regions flanking the Aβ peptides is shown by the letters below the amyloid precursor protein. Each letter represents an amino acid according to the conventional single letter amino acid abbreviation format. Scissile bonds within the amino acid sequence cleaved by the β-, γ-, or α-secretases are indicated by the β, γ, and α labels. Three scissile bonds cleaved by β-secretases which, in combination with scissile bond cleaved by the γ-secretase, produce the $A\beta_{1-40}$, $A\beta_{1-42}$, or $A\beta_{1-43}$ peptide. The three parallel lines below the amino acid sequence identify the amino acid sequences of the $A\beta_{1-40}$, $A\beta_{1-42}$, and $A\beta_{1-43}$ peptides.

This invention provides an assay for the proteolytic activity of secretases, particularly the β-secretase and the γ-secretase that produce the Aβ peptides found in the plaques of AD patients. The method is novel because the activity is detected in a substantially purified preparation of vesicles in which APP protein processing occurs in vivo. Based on that activity assay, new methods are disclosed to isolate the secretases from such substantially purified preparations. Isolating the secretases from the cell organelles in which the APP protein is processed insures that the secretases are the in vivo secretases and not merely a protease from a cell organelle in which such processing does not occur, but which is capable of cleaving the APP protein in vitro. The invention further provides methods of selecting an agent that affects the proteolytic activity of the substantially purified vesicles, the isolated secretase, or the cells containing the vesicles.

As discussed in Example V below, the secretory vesicles of chromaffin cells of the adrenal medulla, herein called "chromaffin vesicles," were discovered to contain Aβ peptides, specifically the $A\beta_{1-40}$ and the $A\beta_{1-42}$ peptides. As such, the chromaffin vesicles were found to contain the in vivo product produced by APP protein processing. Moreover, the vesicles were known to contain the APP proteins and presenilin 1 protein, a protein that affects secretase activity (see Vassilacopoulou et al., *J. Neurochem.* 64:2140–2146, (1995); Tezapsidis et al., *Biochem.* 37(5):1274–1282, (1998); Borchelt et al., *Neuron* 17:1005–1013, (1996); St. George-Hyslop et al., *Science* 264:1336–1340, (1994); Alzheimer's Disease Collaborative Group, *Nature*

Genet. 11:219–222, (1995); and Wasco et al., *Nature Med.* 1:848, (1995)).

Chromaffin vesicles can be obtained in relatively large quantities. That capability, combined with the discovery that the chromaffin vesicles contained the Aβ peptides, permitted for the first time assaying a substantially pure preparation of cell organelles in which APP processing occurs for the proteolytic activity of a secretase. Further, chromaffin vesicles can be obtained in amounts which also permit isolating and sequencing the secretases present in those cell organelles.

As described more fully below in Examples I through IV, bovine chromaffin vesicles were initially discovered to have secretase proteolytic activity. Moreover, it was found that secretases having that activity could be isolated from bovine chromaffin vesicles. But the same methods can be applied to other mammalian species, including humans. As such, secretases from various mammalian species can be assayed for and isolated using the methods disclosed herein.

Further, the amino acid sequence of a bovine secretase is likely to be highly homologous with that of the corresponding human secretase because other bovine proteases are known to have a high degree of homology with the corresponding human protease. For example, the amino acid sequence of the bovine carboxypeptidase H is about 96% homologous with the corresponding human carboxypeptidase H (Hook et al., *Nature,* 295:341–342, (1982); Fricker et al., *Nature,* 323:461–464, (1986); and Manser et al., *Biochem. J.,* 267:517–525, (1990)). Once the amino acid sequence of a secretase from one species is obtained, the corresponding secretase in other species thus can be obtained using recombinant methods such as those described below.

The term "secretase" as used herein means a protease that cleaves an APP protein in vivo. A protease is a protein that enzymatically breaks a peptide bond between two amino acids or an amino acid and chemical moiety as described below. Although the term secretase implies the production of a soluble, secreted peptide, an APP derived product produced by a secretase of the invention need not necessarily be soluble or secreted. "Secretase" includes those secretases referred to as β-secretase and γ-secretase, each of which can relate to one or more protease species that produce the Aβ peptides. "Secretase" also includes the secretase referred to as α-secretase which can relate to one or more protease species that produce the α-APP fragment or the 10 kDa fragment.

The term "vesicles" as used herein refers to secretory vesicles and condensing vacuoles of the secretory pathway. Such vesicles have a membrane that forms a spherical shaped structure and that separates the contents of the vesicles from the rest of the cell. The vesicles process and store their contents until such time as the contents are secreted into the extracellular environment by a cellular process called exocytosis, which occurs by fusion of the secretory vesicle membrane with the cell membrane. The secretion can occur in response to a triggering event in the cell such as a hormone binding to a receptor. Vesicles can be identified by their characteristic morphology or by the presence of a chemical compound characteristic of such vesicles.

As used herein, the term "substantially pure" as used in regard to vesicles means that at least about 80% of the cell organelles in a sample are vesicles. Usually a substantially pure sample has about 95% or more vesicles and often has about 99% or more vesicles. Substantially pure vesicles include a single isolated vesicle. Substantially pure chromaffin vesicles result after approximately an 8-fold purification from the cell homogenate as described below in Example II.

Methods of Determining the Proteolytic Activity of a Secretase

One aspect of the invention is an assay for determining the proteolytic activity of a secretase by obtaining substantially pure vesicles, permeabilizing the vesicles, and incubating the permeabilized vesicles with an APP substrate in conditions which allow the secretase to cleave the APP substrate. The cleavage of the APP substrate is detected and the activity of the secretase is thereby determined.

The vesicles can be obtained from any cell that contains vesicles in which APP protein processing occurs. Vesicles in which such processing occurs can be assayed for by the presence of an Aβ peptide, an α-APP fragment or a 10 kDa fragment in the vesicles using methods described below. Cells containing such vesicles include, for example, neuronal cells from brain tissue, chromaffin cells from adrenal medulla tissue, and platelets from blood. Tissue samples containing such cells can be surgically removed or platelets can be isolated from blood by means known in the art. For tissue samples, the vesicles can be obtained from mechanically homogenized tissue or from tissue disassociated by incubation with collagenase and DNAse (see, for example, Krieger et al., *Biochemistry,* 31, 4223–4231, (1992); Hook et al., *J. Biol. Chem.,* 260:5991–5997, (1985); and Tezapsidis et al., *J. Biol. Chem.,* 270:13285–13290, (1995), which are incorporated herein by reference).

The substantially pure vesicles can be obtained from the tissue homogenates or lysed cells using known methods (see *Current Protocols in Protein Science,* Vol. 1 and 2, Coligan et al., Ed., John Wiley and Sons, Pub., Chapter 4, pp. 4.0.1–4.3.21, (1997)). For example, substantially pure secretory vesicles can be isolated using discontinuous sucrose gradient centrifugation methods (see Krieger et al., ibid.; and Yasothornsrikul et al., *J. Neurochem.* 70, 153–163, (1998)). Vesicles also can be isolated using metrizamide gradient centrifugation (Toomin et al., *Biochem. Biophys. Res. Commun.,* 183:449–455, (1992); and Loh et al., *J. Biol. Chem.,* 259:8238–8245, (1984), or percoll gradient centrifugation (Russell, *Anal. Biochem.,* 113:229–238, (1981). If desired, capillary electrophoresis methods can be used to isolate individual vesicles (Chie et al, *Science,* 279:1190–1193, (1998)). Other methods, including differential centrifugation, fluorescence-activated sorting of organelles, immunoabsorption isolation, elutriation centrifugation, gel filtration, magnetic affinity chromatography, protein chromatographic resins, agarose gel electrophoresis, and free flow electrophoresis methods, also can be used to obtain substantially pure vesicles. The references cited in this paragraph are incorporated by reference.

The purity of the secretory vesicle preparation can be assayed for by morphological or chemical means. For example, vesicles can be identified by their characteristic morphology as observed by electron microscopy. The vesicles can be prepared for electron microscopy using various methods including ultra-thin sectioning and freeze-fracture methods. Vesicles also can be identified by the presence of a characteristic neurotransmitter or hormone present in such vesicles such as the (Met)enkephalin, catecholamines, chromogranins, neuropeptide Y, vasoactive intestinal peptide, somatostatin, and galanin found in chromaffin vesicles (Hook and Eiden, *FEBS Lett.* 172:212–218, (1984); Loh et al., *J. Biol. Chem.* 259:8238–8245, (1984); Yasothornsrikul et al., *J. Neurochem.* 70:153–163, (1998), which are incorporated herein by reference). The presence of the characteristic chemical compound can be determined by various means including, for example, by radioactive, fluorescent, cytochemical, immunological assays, or mass spectrometry methods. More specifically, such assays include radioimmunoassays, western blots or MALDI mass spectrometry. In addition, vesicles can be assayed using light and electron microscopic methods, fluorescent cell activated cell sorter methods, density gradient fractionation methods, immunoabsorption methods, or biochemical methods.

The activity of the secretases can be preserved while the vesicles are purified using known methods. For example, the vesicles can be obtained at a low temperature (e.g. 4° C.) and frozen (e.g. −70° C.) prior to assaying for secretase activity. The activity can also be preserved by obtaining the vesicles in the presence of a stabilizing agent known to preserve protease activity (see *Enzymes*, Dixon et al., Eds., Academic Press, Pub., pp. 11–12, (1979), and *Current Protocols in Protein Science*, Vol. 1 and 2, Coligan et al., Ed., John Wiley and Sons, Pub., Chapter 4, pp. 4.5.1–4.5.36, (1997), which are incorporated herein by reference). Known stabilizing agents include proteins, detergents and salts, such as albumin protein, CHAPS, EDTA, glycerol, and NaCl. Reducing agents are also known to preserve protein function and can be used (see Voet et al., *Biochemistry*, John Wiley and Sons, Pub., pp. 382–388 and 750–755, (1990), which is incorporated herein by reference). Known reducing agents include, for example, β-mercaptoethanol, DTT, and reduced glutathione.

So that secretases within the vesicles are accessible to an APP substrate in an incubation solution, the vesicles are permeabilized (see Voet et al., *Biochemistry*, John Wiley and Sons, Pub., pp. 284–288, (1990); and Krieger et al., ibid., which are incorporated herein by reference). Permeabilizing can result in a continuum of affects on the vesicle ranging from the formation of one or more holes in the membrane to complete lysis of the membrane. Vesicles can be permeabilized, for example, by contact with a detergent or a disruptive agent such as CHAPS, sodium dodecyl sulfate, sodium cholate, digitonin, Brij 30 or TRITON X-100. Vesicles can be lysed, for example, by freeze-thawing, especially in a potassium chloride solution, by suspension in a hypoosmotic solution or by mechanical means such as sonication.

The permeabilized vesicles are incubated with an APP substrate under appropriate conditions for cleavage of the APP substrate by a secretase. Various incubation conditions are known to affect protease cleavage. For example, the pH of the interior of chromaffin vesicles is acidic and some proteases in those vesicles are known to only function in an acidic incubation solution (Pollard et al., *J. Biol. Chem.* 254:1170–1177, (1979); and Hook et al., *FASEB J.* 8:1269–1278, (1994)). Thus, a condition for cleavage of the APP substrate includes an incubation solution having a pH of about 7.0 or less. But secretases in vesicles are released by cells into the extracellular environment, which can have a neutral or basic pH. Thus, vesicles can contain secretases that function at the neutral or basic pH of the extracellular environment and, as such, that pH can also be an appropriate condition. The pH of the incubation solution can be adjusted using known buffers (see Voet et al., *Biochemistry*, John Wiley and Sons, Pub., pp. 35–39, (1990)). Such buffers include, for example, citric acid, sodium phosphate, MES, HEPES and Tris-HCl buffers. The pH of the incubation solution can be determined using known methods such as, pH color indicators in liquid or paper formats, or pH meters. Examples III and IV show that the pH of the incubation solution can affect the activity of secretases.

Other conditions that affect the cleavage include the incubation temperature and incubation time. Proteolytic activity is a function of temperature with excessively low or high temperatures resulting in no detectable activity. An incubation temperature thus is any temperature which allows detection of a cleaved APP substrate. Usually an incubation temperature of about 30° to 45° C., with a typical temperature of about 35° to 40° C., and often a temperature of about 37° C. is used. Although not required, a constant temperature during the incubation time is preferred and can be achieved using an incubator, water bath or other known means. An insufficient or excessive incubation time results in too little production or too much degradation of the product to be detected. The incubation time for cleavage of an APP substrate is that amount of time which allows cleavage of the APP substrate to be detected. A preferred incubation time allows the cleavage of an APP substrate to go to completion, for example, in about 2 to 8 hours.

The proteolytic activity of a secretase is determined by the cleavage of an APP substrate. An "APP substrate" as used herein is a compound having a stereochemical structure that is the same as, or a mimic of, an amino acid sequence in an APP protein, an Aβ peptide, an α-APP fragment or a 10 kDa fragment recognized by a secretase. Thus, an APP substrate for detecting a β- or γ-secretase includes, for example, the $APP_{695}$, $APP_{714}$, $APP_{751}$, and $APP_{771}$ proteins and an APP substrate for detecting an α-secretase includes, for example, those proteins and the Aβ peptides. As discussed above, such proteins, peptides and fragments have been isolated and characterized (Kang et al., *Nature* 325:733–736, (1987); Kitaguchi et al., *Nature* 331:530–532, (1988); Ponte et al., *Nature* 331:525–527, (1988); Tanzi et al., *Nature* 331, 528–530, (1988); Tanzi et al., *Science* 235:880–884, (1987), Glenner et al., *Biochem. Biophys. Res. Commun.* 120, 885–890, (1984); Masters et al., *Proc. Natl. Acad. Sci. USA* 82: 4245–4249, (1985); Selkoe et al., *J. Neurochem.* 146: 1820–1834, (1986); Selkoe, *J. Biol. Chem.* 271:18295–18298, (1996); Mann et al., *Amer. J. Pathology* 148: 1257–66, (1996); Masters et al., *Proc. Natl. Acad. Sci. USA* 82: 4245–4249, (1985); Selkoe et al., *J. Neurochem.* 146: 1820–1834, (1986); Selkoe, *J. Biol. Chem.* 271:18295–18298, (1996); and Mann et al., *Amer. J. Pathology* 148: 1257–66, (1996)).

Such APP substrates can be produced by various methods known in the art (Knops et al., *J. Biol. Chem.* 266:7285–7290, (1991); Hines et al., *Cell. Molec. Biol. Res.* 40:273–284, (1994)). For example, the APP proteins can be made using recombinant technology and cloning the cDNA that encodes the proteins into a suitable expression system. An APP protein cDNA can be obtained, for example, by screening a human brain cDNA library with a DNA probe consisting of an oligonucleotide complementary to the APP protein cDNA, a PCR-generated DNA fragment of the APP protein cDNA, or a DNA fragment of the APP protein cDNA from an expressed sequence tagged (EST) database. Expression systems to produce APP proteins include, for example, *E. coli.*, baculovirus-infected insect cells, yeast cells, and mammalian cells. Alternatively, such proteins can be produced using in vitro methods, which transcribe and translate the RNA that encodes these proteins to produce the proteins. An APP so produced can be purified using methods such as described herein or otherwise known in the art.

An APP substrate is also an APP substrate-fusion substrate, in which a protein or peptide is attached to an APP substrate for the purpose of facilitating the isolation of the APP substrate. Proteins or polypeptides that facilitate purification include, for example, maltose-binding protein and multi-histidine polypeptides attached to the amino or carboxyl terminal end of the APP substrate. Thus, an example of an APP-fusion substrate is a multi-histidine polypeptide attached to the carboxyl terminus of an $APP_{695}$, $APP_{714}$, $APP_{751}$, or $APP_{771}$ protein. Such APP-fusion substrates can be produced using known methods such as by expression of the cDNA that encodes the APP-fusion substrate in a suitable expression system or in vitro translation of the encoding RNA. The APP-fusion substrates so produced can be purified by affinity binding to a column, such as by amylose, nickel or anti-APP antibody column chromatography. Peptides are also known to function as protease substrates (see Sarath et al., *Protease assay methods*, In: *Proteolytic Enzymes, A Practical Approach*, R. J. Beynon and J. S. Bond, Eds., Oxford University Press, Pub., Chapter 3, pp 25–55, (1989). Often such a peptide substrate will contain the amino acids at a scissile bond in a precursor protein (see Benyon et al., *The Schecter and Berger Nomenclature for Protease Substrates*, In: *Proteolytic Enzymes, A Practical Approach*, R. J. Beynon and J. S. Bond, Eds., Oxford University Press, Pub., especially, Appendix 1, pp 231, (1989); and Barrett, *An Introduction to the Proteinases*, In: *Proteinase Inhibitors*, A. J. Barrett and G. Salvesen, Eds., Elsevier, Pub., Chapter 1, pp. 3–18, (1986)). A scissile bond is the peptide bond cleaved by a protease in a precursor protein. The amino acid on the amino terminal side of the scissile bond is often called the P1 amino acid and that on the carboxyl terminal side the P1' amino acid.

A protease that cleaves a scissile bond binds the P1 and P1' amino acids. For some proteases, the P1 amino acid is the primary determinant for protease binding to the precursor protein. For example, the protease trypsin is known to have a marked preference for binding basic P1 amino acids. Peptide substrates often contain the amino acids attached to the amino terminal side of a P1 amino acid because those amino acids can influence the determinant effect of the P1 amino acid.

An APP substrate also includes a peptide having an amino acid sequence recognized by a secretase containing a P1 or P1' amino acid, or both, of a scissile bond in an APP protein and one or more of the amino acids in the APP protein adjacent to either the P1 or P1' amino acids or both. For example, as shown in FIG. 1, a β-secretase scissile bond is between the P1 amino acid methionine (Met or M) and the P1' amino acid aspartic acid (Asp or A). A β-secretase recognition site thus includes, for example, a Met-Asp substrate.

Often an APP substrate is a peptide containing the P1 and P1' amino acids of a scissile bond in an APP protein and the one or two amino acids in the APP protein attached to the amino terminal side of the P1 amino acid. For example, as shown in FIG. 1, a lysine (Lys or K) is attached to the amino terminal side of the P1 amino acid of the β-secretase scissile bond and a valine (Val or V) is attached to the amino terminal side of the Lys. Thus, an APP substrate for the β-secretase includes the Lys-Met-Asp and Val-Lys-Met-Asp (SEQ. ID NO.:1) substrates.

The APP substrate peptide containing the P1 and P1' amino acids of a scissile bond in an APP protein can be determined for the γ-secretase and the α-secretase in the same manner. For example, as shown in FIG. 1, the γ-secretase scissile bond of the $Aβ_{1-40}$ peptide has a Val P1 amino acid, an isoleucine (Ile or I) P1' amino acid, a second Val attached to the amino terminal side of the P1 amino acid and a glycine (Gly or G) attached to the amino terminal side of the second Val. As such, the γ-secretase recognition site for the $Aβ_{1-40}$ peptide includes, for example, the Val-Ile, Val-Val-Ile and Gly-Val-Val-Ile (SEQ ID NO.:2) substrates. The γ-secretase recognition site for the $Aβ_{1-42}$ peptide thus includes, for example, the Ala-Thr, Ile-Ala-Thr and Val-Ile-Ala-Thr (SEQ ID NO.:3) substrates and that the g-secretase recognition site for the $Aβ_{1-43}$ peptide includes, for example, the Thr-Val, Ala-Thr-Val, and Ile-Ala-Thr-Val (SEQ ID NO.:4) sequences. Similarly, the α-secretase recognition site can be determined from the amino acids in the APP protein surrounding the α-secretase scissile bond.

Proteases are known to have endoprotease, aminopeptidase, or carboxypeptidase activity, or a combination of these activities (see Sarath et al., ibid.). A protease having endoprotease activity cleaves the peptide bond between two adjacent amino acids, neither of which is a terminal amino acid, or, as discussed below. between a non-terminal amino acid and a terminal blocking group. A protease having aminopeptidase activity only cleaves the peptide bond between the amino terminal amino acid and its adjacent amino acid. A protease having carboxypeptidase activity only cleaves the peptide bond between the carboxyl terminal amino acid and its adjacent amino acid.

Secretases of the invention also can have endoprotease, aminopeptidase, or carboxypeptidase activity, or a combination of these activities. For example, an Aβ peptide can be cleaved from an APP protein directly by endoprotease cleavage of the scissile bonds at both ends of the β peptide. But an β peptide also can be produced by an endoprotease cleavage of a scissile bond distal to the terminal amino acids of the β peptide followed by aminopeptidase or carboxypeptidase cleavage of the amino acids flanking the terminal amino acids of the Aβ peptide.

An APP substrate often contains one or more amino terminal or carboxyl terminal blocking groups, which prevent aminopeptidase or carboxypeptidase cleavage, respectively (see Sarath et al., ibid.). But an amino terminal blocking group does not prevent carboxypeptidase and, conversely, a carboxyl terminal blocking group does not prevent aminopeptidase cleavage. As such, an APP substrate can often contain both an amino terminal and carboxy terminal blocking group to prevent both aminopeptidase and carboxylpeptidase cleavage. An APP substrate containing both blocking groups can only be cleaved, if at all, by a secretase having endoprotease activity.

Blocking groups and methods of making substrates containing blocking groups are known in the art (see, for example, *Methods in Enzymology*, Vol. 244, "Proteolytic Enzymes," A. J. Barrett, Ed., Chapters 46, 47, and 48, (1994); and Green and Wuts, *Protective Groups in Organic Synthesis*, John Wiley and Sons, Pub., (1991) which are herein incorporated by reference). Amino terminal blocking groups include, for example, acyl (Ac), benzoyl (Bz), succinyl (Suc), carbobenzoxy (Z), p-bromocarbobenzoxy, p-chlorocarbobenzoxy, p-methoxycarbobenzoxy, p-methoxyphenylazocarbobenzoxy, p-nitrocarbobenzoxy, p-phenylazocarbobenoxy, tert-butoxycarbonyl (Boc), benzoyl and the like. Carboxyl blocking groups include, for example, aminomethylcourmarinamide (MCA), the diazomethanes, the p-nitroanlide (pNA), pNA-Tosylate, 2-naphthylamine, the acyloxymethanes, including the (benzoyloxy)methanes, (alkyloxy)methanes, the N,O-diacyl hydroxamates, including the N-aminoacyl-O-4-nitrobenzoyl hydroxamates, esters, including methyl, ethyl and nitrophenyl esters, chloromethylketone and the like.

Although endoproteases do not cleave terminal amino acids, endoproteases can cleave a carboxyl terminal blocking group attached via a peptide bond to the carboxyl terminal amino acid of a peptide containing two or more amino acids (see Sarath et al., ibid.). If the carboxyl terminal amino acid is the P1 amino acid of a scissile bond in a precursor protein, the carboxyl terminal blocking group mimics the P1' amino acid in that scissile bond. Moreover, endoprotease cleavage of the carboxyl terminal blocking group mimics the cleavage of the corresponding scissile bond in the precursor protein.

Such carboxyl terminal blocking groups include, for example, MCA, pNA, and pNA•Tosylate. An APP substrate which contains such a carboxyl terminal blocking group and an amino terminal blocking group can only be cleaved, if at all, by an endoprotease.

An APP substrate includes a secretase recognition site that contains a P1 amino acid of a scissile bond in an APP protein and a carboxyl terminal blocking group which replaces the P1' amino acid in that scissile bond. The APP substrate also contains one or more of the amino acids in the APP protein attached to the amino terminal side of the P1 amino acid. Such an APP substrate will bind a secretase which binds the corresponding scissile bond in the APP protein because the substrate contains the P1 amino acid, the primary determinant for that binding. For example, a β-secretase recognition site containing such a carboxyl terminal blocking group includes, for example, the Val-Lys-Met-MCA substrate in which the MCA group replaces the Asp P1' amino acid of the β-secretase scissile bond. Endoprotease cleavage of the Met-MCA peptide bond in that substrate is equivalent to endoprotease cleavage of the scissile bond Met-Asp of the β-secretase recognition site in the APP protein. Similarly a γ-secretase recognition site for the $A\beta_{1-40}$ peptide includes, for example, the Gly-Val-Val-pNA substrate in which the pNA group replaces the Ile P1' amino acid of the corresponding γ-secretase recognition site and endoprotease cleavage of the pNA group is equivalent to endoprotease cleavage of the corresponding scissile bond in the APP protein. Similar substrates are envisioned for the γ-secretase recognition site for the $A\beta_{1-42}$, and $A\beta_{1-43}$ peptides and the α-secretase recognition site.

The APP substrate as discussed in the paragraph above can also contain an amino terminal blocking group. Only those secretases having endoprotease activity will cleave that APP substrate and the endoprotease cleavage of the substrate will mimic that which occurs in the APP protein. Examples of such APP substrates include, but are not limited to, Z*Lys-Met-MCA, Z*Val-Lys-Met-MCA, Z*Val-Val-MCA, Z*Gly-Val-Val-MCA, Z*Ile-Ala-MCA, Z*Val-Ile-Ala-MCA, Z*Ala-Thr-MCA, and Z*Ile-Ala-Thr-MCA substrates. In these examples, Z represents the amino terminal blocking group carbobenzoxy and the star (*) indicates a non-peptide bond between the Z and the adjacent amino acid. The MCA represents the carboxyl terminal blocking group aminomethylcourmarinamide and the dashes (-) represent peptide bonds between the MCA and the adjacent amino acid or between adjacent amino acids.

Secretases having aminopeptidase activity can be assayed for using an APP substrate that contains an amino acid of a secretase recognition site and a carboxyl terminal blocking group. Examples of such APP substrates include Met-MCA and Lys-MCA substrates from the β-secretase recognition site. However, if such substrates contain only one amino acid, the substrate cannot be cleaved by an endoprotease because the only amino acid is an amino terminal amino acid. The Met-MCA and Lys-MCA substrates were used to identify β-secretase aminopeptidase secretase activities (see Example IV).

An APP substrate often contains one or more labels that facilitate detection of the substrate or the APP derived product. A label can be an atom or a chemical moiety. Substrates containing a label can be made by methods known in the art. For example, radioactive atoms such as $^3H$ or $^{32}P$ can be attached to an APP substrate to detect an APP derived product. Also, heavy atoms or atom clusters such as, gold clusters can be attached. Moreover, fluorescent molecules such as, fluorescein, rhodamine, or green fluorescent protein, can be attached. A label can have more than one function. For example, the MCA is a carboxyl blocking group that is not fluorescent when bound in an APP substrate, is an APP derived product when cleaved by an endoprotease from a substrate, and is a label because, when MCA is cleaved from the substrate, it becomes fluorescent aminomethylcourmarinamide (AMC or free MCA) which is detectable (Azaryan and Hook, Arch. Biochem. Biophys. 314:171–177, (1994); and Azaryan et al., J. Biol. Chem. 270:8201–8208, which are incorporated herein by reference).

Cleavage of an APP substrate can be detected by the presence of an APP derived product. The term "APP derived product" refers to a protein, polypeptide, peptide or chemical moiety produced by proteolytic cleavage of an APP substrate. An APP derived product includes, for example, an Aβ peptide, an A-APP fragment, a 10 kDa fragment, and AMC. A chemical moiety is the blocking group or label discussed above.

An APP derived product or an APP protein can be qualitatively or quantitatively detected using various methods. For example, these products or proteins can be detected by an immunoassay using antibodies such as monoclonal or polyclonal antibodies against the $A\beta_{1-40}$ peptide, $A\beta_{42}$ peptide, $A\beta_{1-43}$ peptide, the amino terminal or the carboxyl terminal regions of the APP proteins and the APP proteins. Such antibodies are commercially available, for example, from PENINSULA LABORATORIES, Belmont, Calif.; CALBIOCHEM, San Diego, Calif.; QCB, Hopkinton, Mass.; or IMMUNODYNAMICS, La Jolla, Calif.

SDS-PAGE electrophoresis and western blots can also be used to detect an APP derived product and an APP protein. Other methods include detecting a label on or from the APP derived product or APP protein such as a radioactive or fluorescent label. Microsequencing, amino acid composition analysis, or mass spectrometry analysis can also be used. Chromatography separation methods based on physical parameters such as molecular weight, charge, or hydrophobicity can be used. Preferred chromatography methods include high pressure liquid chromatography (HPLC) and automated liquid chromatography (FPLC, PHARMACIA, Piscataway, N.J.). Spectrophotometric detection methods such as UV absorbance at 280 nm or 210–215 nm, can also be used. Known light or electron microscopic methods as well as fluorescent activated cell sorter methods also can be used to detect APP derived products and APP proteins. The quantitative fluorescence analysis using a fluorometer was used to detect the fluorescent AMC product produced by β-secretase cleavage of the Z*Val-Lys-Met-MCA, Met-MCA, and Lys-MCA (see Examples III and IV).

FIG. 2 shows the endoprotease cleavages that can occur in an APP substrate containing a β-secretase recognition site and amino and carboxyl terminal blocking groups and how such cleavages can be detected. In that figure, the three endoprotease cleavages of the APP substrate Z*Val-Lys-Met-MCA are shown (#1, #2, and #3). The Met-MCA bond (#3) mimics the scissile bond between the P1 and P1' amino acids Met and Asp in the APP protein at the amino terminal end of the Aβ peptide. Endoprotease cleavage of the Met-MCA bond in the substrate is equivalent to endoprotease cleavage of the APP protein. That cleavage in the APP protein would produce directly the amino terminal end of the Aβ peptide. That cleavage can be detected by the characteristic fluorescence produced by AMC (free MCA).

Endoprotease cleavage of the Lys-Met bond (#2) and the Val-Lys bond (#3) in the Z*Val-Lys-Met-MCA substrate produces a Met-MCA and Lys-Met-MCA peptide, respectively. The corresponding endoprotease cleavages in the APP proteins would be distal to the amino terminal end of the β peptide. However, such distal endoprotease cleavages can occur in vivo because, as discussed above, such cleavages followed by aminopeptidase cleavage of the flanking amino acids can produce the amino terminal end of the β peptide.

The Met-MCA and Lys-Met-MCA peptides are not fluorescent, but contain free amino terminal amino acids, which an aminopeptidase can cleave to liberate AMC. To insure that the endoprotease cleavages of the Lys-Met and the Val-Lys bonds are detected, an aminopeptidase can be added to an incubation solution to liberate AMC from the Met-MCA and Lys-Met-MCA peptides. Known aminopeptidases include, for example, aminopeptidase M and methionine aminopeptidase (*Mammalian Proteases, a Glossary and Bibliography*, J. K. Mcdonald and A. J. Barrett, Ed., Academic Press, Pub., p. 23–99, (1986)). In this manner, all the endoprotease cleavages of the Z*Val-Lys-Met-MCA substrate can be detected.

Such methods were used to identify endoprotease activity of one or more β-secretases in substantially purified vesicles (see Example III). In particular, a secretase in substantially purified vesicles was shown to cleave the Z*Val-Lys-Met-MCA substrate at a pH of about 4.0 to about 5.5 using these methods.

Methods of Isolating a Secretase

The present invention also is directed to a method of isolating a secretase using the assay described above to determine the proteolytic activity of a secretase and isolating that secretase from substantially purified vesicles. Generally, the isolation is done by assaying the activity of the secretase after each step in the isolation. If necessary, the activity can be preserved during the isolation procedure using methods such as those described above, including, for example isolating the secretase at a low temperature (e.g. 4° C.), or in the presence of one or more of the above-described reducing or stabilizing agents.

The secretase is isolated based on its physical properties. For example, a secretase can be isolated based on its molecular weight and size using gel filtration chromatography such as, Sephacryl S200, Sephadex G150, Superose 6 or 12, and Superdex 75 or 200 resin chromatography. A secretase can also be isolated based on its charge using ion-exchange chromatography such as DEAE-Sepharose, CM Sephadex, MonoQ, MonoS and MonoP resin chromatography. In addition, a secretase can be isolated based on its water solubility using hydrophobicity chromatography such as phenyl Sepharose, butyl Sepharose and octyl Sepharose resin chromatography. Interactions between the secretase and hydroxyapatite can also be used for isolation using, for example, macro-prep hydroxyapatite, and Bio-Gel HT hydroxyapatite resins.

A secretase can also be isolated based on specific biochemical properties of the secretase using affinity chromatography. For example, the secretase can be isolated using APP substrate affinity chromatography under conditions in which the secretase binds the APP substrate but does not cleave it. Glycosylated secretases can be isolated using lectin affinity chromatography such as, concanavalin A-Sepharose, lentil lectin Sepharose, wheat germ lectin Sepharose resin chromatography. The proteolytic activity of sulfhydryl groups such as those on cysteine amino acids can be used to isolate the secretases using thiol-propyl chromatography. Finally, the affinity of the secretases for specific dyes can be used for separation such as, blue-Sepharose resin chromatography. Other affinity chromatography methods include arginine-Sepharose, benzamidine Sepharose, glutathione Sepharose, lysine-Sepharose and chelating Sepharose resin chromatography. The secretases can also be isolated by non-chromatographic fractionation methods using, for example, native gel electrophoresis, analytical ultracentrifugation and differential ammonium sulfate precipitation methods.

Using such methods, alone or in combination, a secretase of the invention can be isolated. The term "isolated" when used in reference to a secretase means that the secretase is relatively free of other proteins, amino acids, lipids and other biological materials normally associated with a cell. Generally, an isolated secretase constitutes at least about 50%, and usually about 70% to 80%, and often about 90 to 95% or more of the biological material in a sample. A secretase often is isolated such that it is free of other substances that affect the cleavage of an APP substrate, such as an inhibitor or activator protein. The extent to which the secretases are isolated using such methods can be determined by known protein assays. For example, the amount of protein in the resulting chromatographic fractionation can be quantitated using the Lowry method and the specific activity can be used to quantitate the isolation. Alternatively, SDS-PAGE or two-dimensional gel electrophoresis and mass spectroscopy methods can be used.

After initial isolation of a secretase, antibodies specific to the secretase can be produced and secretases isolated using immunoaffinity chromatography. Such antibodies can be produced using known immunological methods including, for example, monoclonal antibody and polyclonal antibody production methods (see Haylow and Lane, *Antibodies: A Laboratory Manual*, Cold Spring Harbor Laboratory Press, (1988)).

The amino acid sequence of the secretase also can be determined after isolation of the secretase. For example, the amino acid sequence of the secretase can be determined using peptide microsequencing methods known in the art (see "*Current Protocals in Protein Science*," Vol. 1 and 2, Coligan et al., Ed., (1997), John Wiley and Sons). Alternatively, the partial amino acid sequence can be determined from fragments of the secretase using mass spectrometry and Edman microsequencing methods ("*Current Protocols in Protein Science*," Vol. 1 and 2, Coligan et al., Ed., (1997), John Wiley and Sons). For example, the secretase can be isolated using an SDS-PAGE gel and stained with coomassie blue in the gel. The secretase in the gel can be subjected to in-gel tryptic digestion and the amount of protein determined by amino acid analysis. Tryptic peptide fragments can be separated by HPLC, and the amino acid sequence of each fragment determined by Edman microsequencing and mass spectrometry methods. The amino acid sequence of the secretase can be determined from the amino acid sequences of the peptide fragments using computer analysis of known amino acid sequences.

Based on the partial amino acid sequence of a secretase, the cDNA of the secretase can be cloned (see, for example, *Molecular Cloning, a Laboratory Manual*, Vol. 1, 2, and 3, Sambrook et al., Ed., Cold Spring Harbor Laboratory Press, Pub., (1989); and *Current Protocols in Molecular Biology*, Vol. 1, 2, and 3, Ausubel et al., Ed., Wiley Interscience, Pub., (1997)). Briefly, partial, cloned secretase cDNAs are obtained by reverse transcription-polymerase chain reaction methods (RT-PCR) using oligonucleotides complementary to the partial amino acid secretase sequences. The complementary oligonucleotides synthetically synthesized can contain either degenerate codons, including inosine, or be optimized for mammalian cell use. The PCR-generated DNA fragment is analyzed for nucleic acid sequences and restriction enzyme sequences, and overlapping sequences among the different PCR-generated DNA fragments are determined. Northern blot or RT-PCR analysis using the PCR-generated cDNAs, or complementary oligonucleotides, so produced are used to determine tissues that produce mRNAs encoding the secretase. A cDNA library from such tissues is constructed and screened using the PCR-generated secretase cDNA or the complementary oligonucleotides. From such screened cDNA libraries, the cDNA sequence encoding the full-length amino acid sequence of the secretase is determined.

The cDNA of a secretase can also be obtained by generating antibodies against the partial amino acid sequences, screening cDNA expression libraries with an anti-secretase antibody, and analyzing the nucleic acid sequences of such clones. The amino acid sequence of the secretase can be deduced from the secretase cDNA sequence. The full-length cDNA can be cloned in an expression system such as in *E. coli*, Sf9 insect cells, yeast, or mammalian cell lines, and the activity of the expressed secretase determined to confirm that the cDNA encodes a functional secretase.

Another method of obtaining the cDNA of a secretase is to clone the secretase in a genetic screen for isolating the secretase cDNA using the bacteriophage 1 regulatory circuit, where the viral repressor is specifically cleaved to initiate the lytic phase of bacteriophage to allow detection and isolation of plaques containing the secretase cDNA(s) (Sices and Kristie, *Proc. Natl. Acad. Sci. USA* 95:2828–2833, (1988)).

The gene(s) encoding a secretase can be isolated by screening a genomic library with the cDNAs encoding the partial or full length secretase, or with the oligonucleotides that are complementary to a sequence encoding a determined secretase amino acid sequence. The nucleic acid sequence of the secretase genomic DNA is determined, and the exon/intron structure of the secretase gene is determined by comparing the DNA sequence of the gene to the nucleic acid sequence of the secretase cDNA.

Once the cDNA encoding a partial or full-length endogenous secretase is obtained from one animal species, that cDNA can be used to obtain endogenous secretases from another animal species using known methods (*Molecular Cloning, a Laboratory Manual*, ibid.; and *Current Protocols in Molecular Biology*, ibid.). For example, the cDNA encoding the partial bovine secretase can be used to obtain cDNAs encoding human secretases. Briefly, a partial or full-length bovine cDNA, or a labeled complementary oligonucleotide, is used to isolate the human secretase cDNA by screening human cDNA libraries constructed from tissues that contain secretase mRNA, determined by northern blot or RT-PCR analyses. Alternatively, the human secretase cDNA can be obtained by searching the expressed sequence tag database (EST) for human cDNA sequences similar to the bovine secretase cDNA. DNA sequencing of the resulting secretase clones can be performed to determine the nucleic acid sequence encoding the human secretase and the corresponding amino acid sequence can be deduced. The cDNA encoding the human secretase can be cloned in and expressed by a suitable expression vector and the activity of the expressed secretase can be determined. The genes encoding the human secretase can be cloned as described herein.

The nucleic acid sequence of a secretase can also be used to produce the secretase using known recombinant methods (*Molecular Cloning, a Laboratory Manual*, ibid.; and *Current Protocols in Molecular Biology*, ibid.). The cDNA encoding the secretase can be inserted into an appropriate expression vector and the expression vector introduced into an appropriate host as described herein. Expression of the secretase by the host is stimulated by expression of a vector promotor.

Methods of Screening for Agents that Affect the Proteolytic Activity of a Secretase Another aspect of the invention is a method of selecting an agent that alters the cleavage of an APP substrate by a secretase. Such agents, particularly those that decrease the cleavage by the β-secretase and γ-secretases or that increase the cleavage by the α-secretase, are useful for developing drugs that prevent or treat AD. Agents having divergent chemical structures can be assayed using such methods including, for example, small organic molecules that optionally contain heteroatoms or metals, amino acids, peptides, polypeptides, proteins, peptidomimetics, nucleic acids, carbohydrates, glycoproteins, lipids, and lipoproteins.

The method is based on comparing the APP substrate cleavage, or the APP protein, or APP derived product production that occurs with and without an agent. This is achieved by determining the APP substrate cleavage or the APP protein or the APP derived product produced in a first incubation or culture solution lacking the agent and comparing that result with that which occurs in a second incubation or culture solution containing the agent. The first and second incubation or culture solutions can be different solutions or the same solution to which the agent is added or removed. The APP substrate cleavage, the APP protein, and the APP derived product can be assayed using the methods described herein. The concentration of the agent can vary due to parameters known in the art such as the hydrophobicity, charge, size and potency of the agent, but typically is about a $10^{-9}$ to $10^{-3}$ M.

Agents are selected that alter the cleavage of an APP substrate or production of an APP protein or an APP derived product. The cleavage or production is altered if the agent causes a significant change in the cleavage or production relative to that which occurs without the agent. A significant change can be determined using a variety of qualitative or quantitative methods, such as, for example, by a visual or statistical analysis of the comparison data. For example, the mean amounts of an APP derived product obtained with and without the agent can be analyzed using a two-sided Student's t-test and a $p \geq 0.02$ or greater, and preferably a $p \geq 0.05$, in that test can be indicative of a significant difference.

Often agents are screened using substantially pure vesicles as the source of the secretase. But substantially pure vesicles can contain, in addition to secretases, other substances that affect the cleavage of an APP substrate, such as the presenilin 1 protein. Thus, a screen using such vesicles selects for agents that directly or indirectly alter the cleavage. An agent can directly affect the cleavage by, for example, inhibiting the binding of an APP substrate to a secretase. But an agent can also indirectly alter the cleavage by affecting an inhibitor or activator substance which in turn affects the activity of the secretase. For example, proteases may be present in the vesicle that produce the secretase from a precursor protein or that degrade the secretase. An agent thus can indirectly affect the secretase activity by affecting the proteases which produce or degrade the secretase. Often permeabilized chromaffin vesicles and an APP protein, Aβ peptide, Z*Val-Lys-Met-MCA, Z*Gly-Val-Val-MCA, Z*Val-Ile-Ala-MCA, or Z*Ile-Ala-Thr-MCA substrate are used in the assay.

An isolated secretase, obtained as described above, can also be used to select for agents that affect the activity of the secretase. Using an isolated secretase free of other substances that affect the cleavage of an APP substrate, agents can be selected that directly affect cleavage of the APP substrate. The affect of an agent on such an isolated secretase and on substantially purified vesicles can be compared to determine the direct and indirect affects of the agent. Moreover, that comparison can be used to determine if the vesicles contain inhibitors or activators of the secretase removed during isolation of the secretase.

The protease class to which an isolated secretase belongs can be determined using agents known to selectively inhibit different classes of proteases. For example, E-64c, cystatin, and p-mercuribenzoate inhibit cysteine proteases; phenylmethylsulfonyl fluoride (PMSF), soybean trypsin inhibitor, and $\alpha_1$-antitrypsin inhibit serine proteases; ethylenediaminetetraacetic acid (EDTA) and 1,10-O-phenanthroline inhibit metalloproteases; and pepstatin A inhibits aspartyl proteases.

In another method, a cell containing vesicles having the proteolytic activity of a secretase is used to select for an agent. Cells containing such vesicles can be identified using the methods described above to determine the proteolytic activity of a secretase in the vesicles. The cells are cultured in a first culture solution without the agent and in a second culture solution with the agent and the production of an APP protein or an APP derived product by the cell, especially an Aβ peptide, α-APP fragment or 10 kDa fragment, in the first and second culture solution compared.

A problem with using transformed cell cultures or cell lines to select agents is that the agents may be ineffective in vivo because cells in culture can process a protein in a manner unrelated to that which occurs in vivo. Thus, agents that affect the processing of such cells are ineffective because the processing that they affect does not occur in vivo. The cell based method provided in the present invention avoids this problem by selecting cells determined to contain vesicles that have the proteolytic activity of a secretase. As such, the method insures that the cells process the APP protein in the cell organelle in which that processing occurs in vivo.

A cell used in this method can be obtained from a variety sources. For example, disassociated cells maintained in a primary culture can be used in the method. Such disassociated cells can be maintained in a primary culture using known methods (see, for example, Hook et al., ibid.; and Tezapsidis et al., ibid.). Disassociated cells have the advantage of retaining many of the functional characteristics that they have in the tissue that they are obtained from. But primary cultures of disassociated cells generally die after a period of time. Cell lines, transformed cells and cloned cells, on the other hand, have the advantage of being immortal. But such cells are known to often abnormally process proteins. As such, it is particularly important to use immortalized cells that are determined to contain vesicles in which the proteolytic activity of a secretase occurs so as to insure that the cells are processing the APP protein in the same manner as in vivo. Various cell transformation methods can be used to obtain such cells (see for example, Alarid et al. *Development,* 122(10):3319–29, (1996); and Schecter et al., *Neuroendocrinology,* 56(3):300–11, (1992), which are incorporated herein by reference). A chromaffin cell, either obtained by disassociation or by transformation, is often used in this method.

In the cell based assay of the present invention, the agent is often present when the cells are producing an APP derived product because some agents are known to only affect a protease in a cell when the protease is producing a product. For example, agents are known to inhibit enkephalin production in chromaffin cells only when the chromaffin cells are actively producing enkephalin (Tezapsidis et al., ibid.). Various methods can induce cells to produce proteolytically processed peptides in vesicles. For example, proteolytic processing can be induced by exocytosis. Exocytosis can be induced by various means including, for example, by increasing the extracellular potassium chloride concentration or by binding nicotinic cholinergic receptors on cells with nicotine. Proteolytic processing of the A: peptides can also be induced by stimulating protein kinase with phorbol esters (Koo, *Molec. Medicine,* 3:204–211, (1997); and LeBlanc et al., *J. Neurosci.,* 18:2908–2913, (1998)).

For example, chromaffin cells can be induced to produce an Aβ peptide by culturing the cells in potassium chloride (about 5 to 500 mM), nicotine (about $10^{-3}$ to $10^{-6}$ M), or phorbol ester (about $10^{-3}$ to $10^{-6}$ M) for a sufficient amount of time to stimulate production (about 1 to 72 hours for the nicotine and potassium chloride and about 12 to 96 hours for the phorbol ester). During active production of the Aβ peptide by the cells, an agent is incubated with the chromaffin cells under appropriate conditions and for an appropriate amount of time (e.g. about 2 to 8 hours). The cells can then be lysed and the production of an Aβ peptide with and without the agent compared. To facilitate that comparison, a protease inhibitor such as, chymostatin, leupeptin, and soybean trypsin inhibitor (STI), can be added when cells are lysed to prevent non-specific digestion of the Aβ peptide by non-specific proteases released by cell lysis.

The cell based assay can be used to select an agent that affects cell expression. For example, the expression of a nucleic acid that encodes a secretase can be tested in such an assay. Inhibitors of gene transcription, such as actinomycin D or an antisense nucleic acid, or agents that modify protein transcription factors that regulate gene expression, such as steroids, also can be tested. The cell based assay can also be used to select agents that affect protein processing, including those affecting RNA splicing, RNA polyadenylation, RNA editing, protein translation, signal peptidase processing, protein folding including chaperone-mediated folding, disulfide bond formation, glycosylation, phosphorylation, covalent modification including methylation, prenylation, and acylation, and association with endogenous protein factors that modify secretase activity.

Agents found to alter cleavage of an APP substrate can be evaluated in vivo using transgenic AD animal models. Transgenic animal models have been developed in which the animals have brain amyloid plaques containing Aβ peptides and, in some models, exhibit cognitive deficits such as excessive memory loss. Exemplary transgenic animals include mice that contain the Indiana mutation of the human APP cDNA under the control of the PDGF promoter (Johnson-Wood et al., *Proc. Natl. Acad. Sci., USA,* 94:1550–1555, (1997)). These mice express increased levels of brain At peptides and amyloid plaques and show cognitive deficits. Another exemplary transgenic animal is a mouse strain containing the Swedish mutation of the human APP-695 cDNA with the hamster PrP promoter (Hsiao, J. Neural Transmission, 49:135–144, (1997)). These mice express increased levels of brain Aβ peptides, have amyloid plaques and are memory impaired.

Agents can be administered to such animals using methods known in the art, particularly those methods that result in the agent traversing the blood brain barrier. For example, such agents can be administered by direct injection into the central nervous system or by administration with a minipump. Agents that naturally traverse the blood brain barrier can be systematically administered by intravenous, subcutaneous, or oral routes. Such agents can be administered in effective doses which for example can range from 0.001 to 10 mg/kg body weight. Agents can be administered prophylactically or therapeutically in single or multiple dose schedules.

Agents can be assayed by histopathological examination of the brains from such transgenic animals. For example, quantitative, microscopic analysis of amyloid plaque formation can be used to determine the effect of the agent. Agents which reduce the size or frequency of amyloid plaques are preferred. In addition, agents can be assayed by measuring brain levels of $A\beta_{1-40}$, $A\beta_{1-42}$, or $A\beta_{1-43}$ by radioimmunoassay or ELISA. Agents that reduce $A\beta_{1-40}$, $A\beta_{1-42}$, or $A\beta_{1-43}$ levels are preferred. Agents also can be assayed for their effect on the cognitive behavior of such animals using known methods. For example, the memory capability of mice can be determined using the water maize test. Agents which enhance the memory capability are preferred.

Agents that effectively reduce or inhibit $A\beta$ peptide production or amyloid plaque formation or increase memory in any of the methods described above can be used to treat or prevent AD. Persons identified as probable AD patients by known medical methods can be administered such agents. Also, people diagnosed as having a high probability of developing AD can be administered such agents. Patients are assessed for improvement in cognitive abilities. Upon autopsy, brain tissue is assessed for amyloid plaques and $A\beta$ levels. Agents are administered by known methods such as those described above for the animal model.

Agents that effectively reduce or inhibit $A\beta$ peptide production or amyloid plaque formation or increase memory can also be used to enhance memory function of people, especially the elderly. People can be administered such agents and assayed for improved memory capability. Agents can be administered by known methods such as those described above for the in vivo assay.

The following examples are intended to illustrate but not limit the present invention.

EXAMPLE I

Isolation of Chromaffin Vesicles

Chromaffin vesicles were isolated from fresh bovine adrenal medulla by discontinuous sucrose gradient centrifugation (Krieger et al., *Biochemistry*, 31, 4223–4231, (1992); Yasothornsrikul et al., *J. Neurochem.* 70, 153–163, (1998)). Briefly, fresh bovine adrenal glands were dissected to obtain the medulla region. These medulla from 40 glands were homogenized in 200–250 ml ice-cold 0.32 M sucrose, and the homogenate was centrifuged at 1,500 rpm in a GSA rotor (Sorvall centrifuge) for 20 minutes at 4° C.

The resultant supernatant was collected and centrifuged at 8,800 rpm in a GSA rotor (Sorvall centrifuge) for 20 minutes at 4° C. to obtain a pellet of chromaffin vesicles. The pellet of chromaffin vesicles was washed three times in 0.32 M sucrose. Each wash consisted of resuspending the pellet of chromaffin vesicles with an equal volume (same volume as original homogenate) of 0.32 M sucrose and centrifugation at 8,800 rpm in a GSA rotor to collect the vesicles as the pellet.

After washing, the chromaffin vesicles were resuspended in 120 ml of 0.32 M sucrose and subjected to discontinuous sucrose gradient centrifugation. For that centrifugation, 10 ml of the washed chromaffin vesicle suspension was layered on top of 25 ml of 1.6 M sucrose in each of 12 centrifuge tubes. The 12 tubes of sucrose gradient were centrifuged in a SW28 rotor at 25,000 rpm for 120 minutes at 4° C. The pellets of isolated chromaffin vesicles from 12 tubes were resuspended in 12 ml of 0.015 M KCl with a glass-glass homogenizer, and stored at −70° C., prior to use. A chromaffin vesicle lysate was prepared by freeze-thawing the isolated chromaffin vesicles in the 15 mM KCl.

EXAMPLE II

Assay for Chromaffin Vesicles

The chromaffin vesicles in the Example I preparation were assayed for the chromaffin vesicle markers (Met) enkephalin, catecholamines, the lysosomal marker acid phosphatase and total protein. Fractions containing the highest amount of chromaffin vesicle markers were identified as chromaffin vesicles. The homogeneity of the chromaffin vesicles was approximately 99% as assayed by the proteolytic activity of the chromaffin vesicle markers (Met) enkephalin and catecholamines and the absence of the lysosomal marker acid phosphatase. Electron microscopy showed that uniform, homogeneous, and intact chromaffin vesicles were isolated. The chromaffin vesicles were purified approximately 8-fold from the cell homogenate based on the measurement of the picograms of (Met)enkephalin per microgram of protein in the samples.

EXAMPLE III

β-Secretase Endoprotease Activity

The APP substrate, Z*Val-Lys-Met-MCA, was used to identify a β-secretase based on endoprotease activity. That substrate was commercially obtained and had a purity of 99% or better as determined by the manufacturers (PENINSULA LABORATORIES, Belmont, Calif. and PHOENIX LABORATORIES, Mountain View, Calif.).

The β-secretase endoprotease activity was identified by incubating the chromaffin vesicle lysate (2–10 μl, of 10–20 mg protein/ml) with the Z*Val-Lys-Met-MCA substrate (100 μM final concentration) and detecting AMC fluorescence. The chromaffin vesicle lysate was prepared as described in Example I. The endoprotease activity was determined as a function of pH by varying the pH of the incubation solution between 3.0 to 8.0 in 0.5 pH increments. Citric acid, sodium phosphate, and Tris-HCl buffers (100 mM final concentration) were used to adjust the pH of the incubation solutions between 3.0 to 5.5, 6.0 to 7.5, and 8.0, respectively. Duplicate samples at each pH increment (100 μl each) were distributed among 22 wells in a covered microtiter well plate and incubated at 37° C. for 8 hours in a water bath.

As discussed above, endoprotease cleavage between the Met-MCA bond in the Z*Val-Lys-Met-MCA substrate produces fluorescent AMC, but endoprotease cleavage between the Lys-Met or Val-Lys bonds in that substrate produces non-fluorescent Lys-Met-MCA and Met-MCA peptides. To insure that the latter two endoprotease cleavages were detected, aminopeptidase M (20 μg/ml final concentration, BOEHRINGER MANNHEIM) was added to each incubation solution to produce fluorescent AMC from the Lys-Met-MCA and Met-MCA peptides. Prior to adding the aminopeptidase M, each incubation solution was adjusted to pH 8.3 using Tris-HCl because aminopeptidase M functions at a basic pH. A second incubation at 37° C. for 1 hour in the water bath was conducted to complete the aminopeptidase M reaction.

Upon termination of that second incubation, AMC fluorescence was assayed using a fluorometer (IDEXX fluorometer, FCA Fluorescence Concentration Analyzer, cat. no. 10-105-2, BAXTER HEALTH CARE CORP., Mundelein, Ill.) at excitation and emission wavelengths of 365 and 450 nm, respectively. Standard AMC concentrations were also measured to quantitate relative fluorescence with the molar amount (pmol) of AMC generated by the secretase. The resulting AMC fluorescence reflects the endoprotease activity in cleaving either the Met-MCA, Lys-Met. and Val-Lys bonds in the Z*Val-Lys-Met-MCA substrate.

Figure 3:
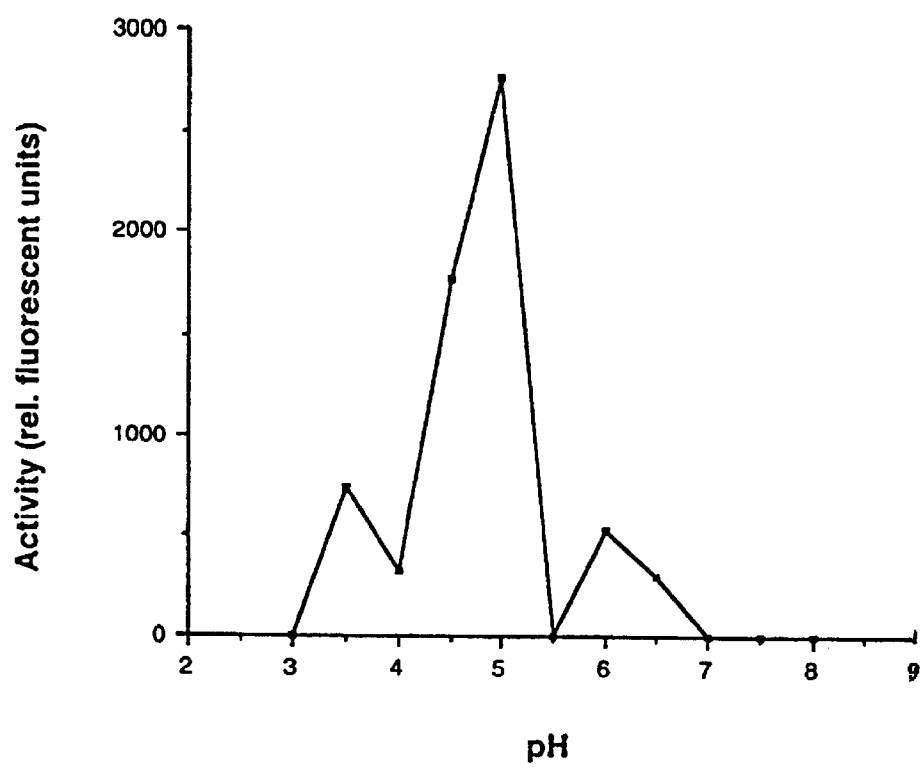

The AMC fluorescence was plotted as a function of pH and is shown in FIG. 3. Analysis of that plot shows a principal β-secretase endoprotease activity having a pH optimum of about 4.5–5.0. In addition, the plot shows two lesser β-secretase endoprotease activities having pH optimums of about pH 3.5 and 6.0–6.5.

EXAMPLE IV

β-Secretase Aminopeptidase Activity

The APP substrates, Met-MCA, and Lys-MCA, were used to identify a β-secretase based on aminopeptidase activity. Those substrates were commercially obtained and had a purity of 99% or greater as determined by the manufacturers (PENINSULA LABORATORIES, Belmont, Calif. and PHOENIX LABORATORIES, Mountain View, Calif.).

The β-secretase Met aminopeptidase activity was identified by incubating the chromaffin vesicle lysate (5 μl, of 10–15 mg/ml) with the Met-MCA substrate (100 mM final concentration) and detecting the resulting AMC fluorescence. The chromaffin vesicle lysate was prepared as described in Example I. The aminopeptidase activity was determined as function of pH by varying the pH of the incubation solution between 3.0 to 8.0 in 0.5 pH increments. Citric acid, sodium phosphate, and Tris-HCl buffers (100 mM final concentration) were used to adjust the pH of the incubation solutions between 3.0 to 5.5, 6.0 to 7.5, and 8.0, respectively. Duplicate samples at each pH increment (100 ml each) were distributed among 22 wells in a covered microtiter well plate and incubated at 37° C. for 4 hours in a humidified incubator.

Similarly, the β-secretase Lys aminopeptidase activity was identified by incubating the chromaffin vesicle lysate (5 μl of 10–15 mg/ml) with the Lys-MCA substrate (100 μM final concentration) and detecting the resulting AMC fluorescence. The incubation was identical to that described for the Met aminopeptidase assay except that the incubation time was 2 hours long.

Upon termination of the incubations, AMC fluorescence was assayed as described above. The resulting AMC fluorescence indicating β-secretase Met and Lys aminopeptidase activities was plotted as a function of pH and is shown in FIGS. 4 and 5, respectively.

Figure 4:
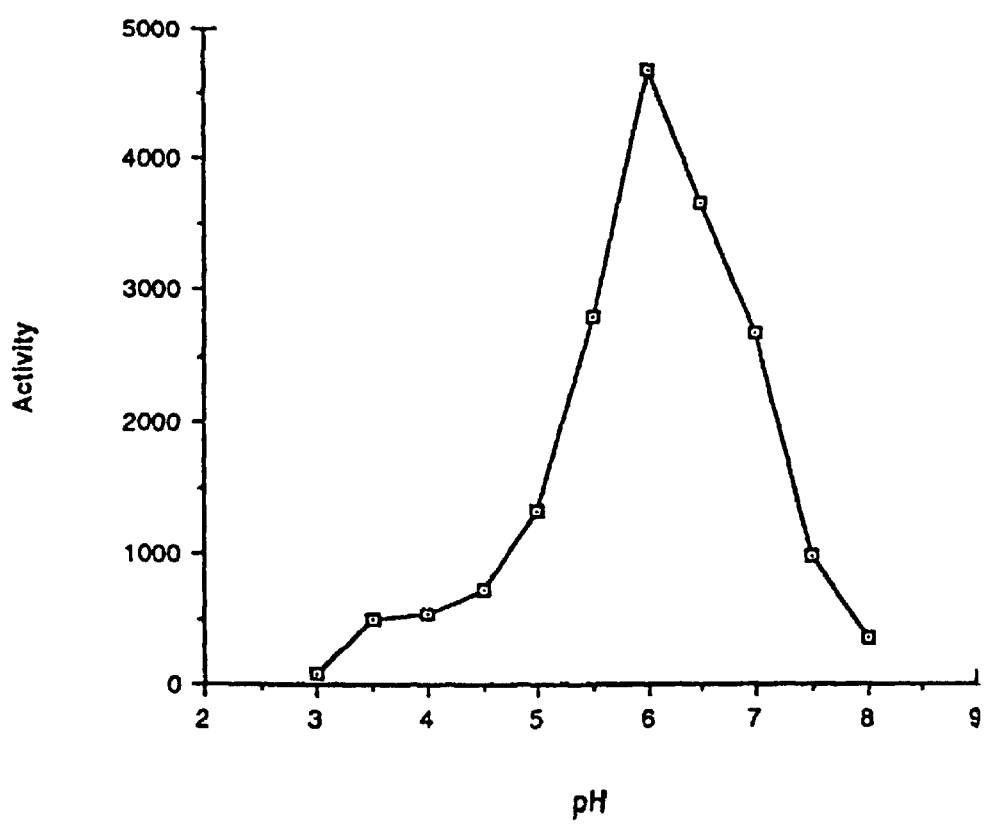
FIG. 4. The fluorescence activity is plotted as a function of the pH at which a lysate of substantially pure chromaffin vesicles is incubated with the Met-MCA substrate. The fluorescence activity is the relative fluorescence of the free MCA (AMC) released by proteolytic cleavage of the substrate.
Figure 5:
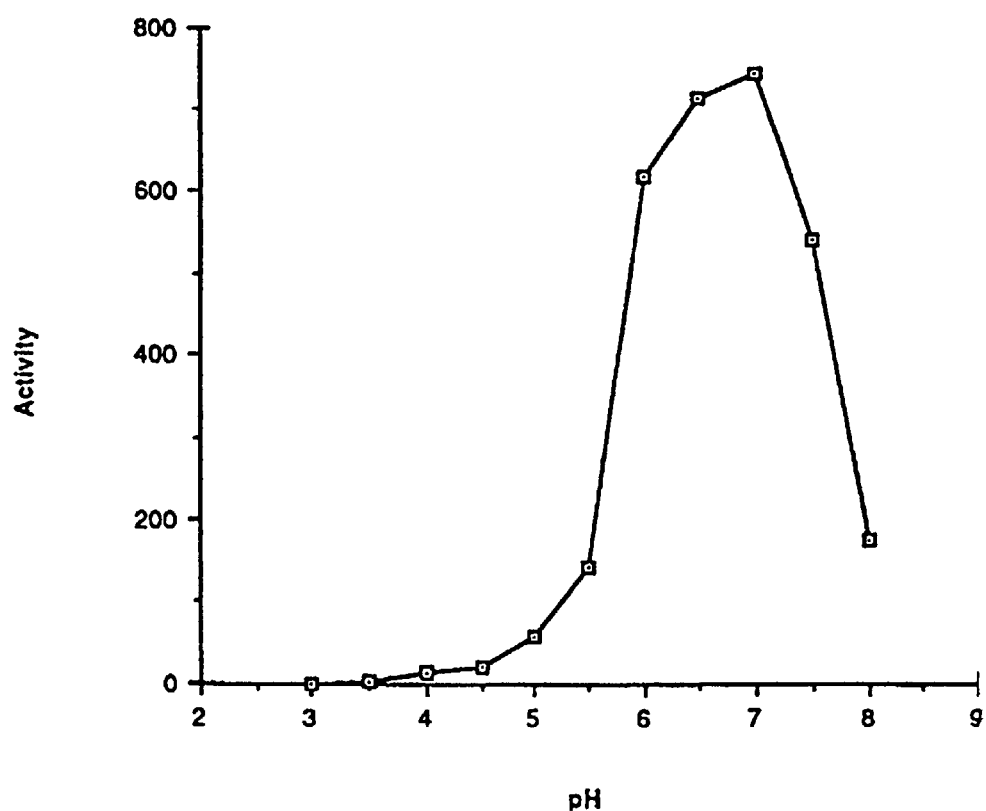
FIG. 5. The fluorescence activity is plotted as a function of the pH at which the lysate of substantially pure chromaffin vesicles is incubated with the Lys-MCA substrate. The fluorescence activity is the relative fluorescence of the free MCA (AMC) released by proteolytic cleavage of the substrate.

Analysis of FIG. 4 shows a β-secretase Met aminopeptidase activity having a pH optimum of about 5.5–6.5. Similarly, analysis of FIG. 5 shows a β-secretase Lys aminopeptidase activity having a pH optimum of about 6.0–7.0.

EXAMPLE V

Identification of Aβ Peptides

The chromaffin vesicle lysate was analyzed for the proteolytic activity of AZ peptides using commercially available polyclonal and monoclonal antibodies against the $A\beta_{1-40}$ and $A\beta_{1-42}$ (PENINSULA LABORATORIES, Belmont, Calif. and QCB, Hopinton, Mass., respectively) in known radioimmunoassay (RIA) and ELISA methods. The chromaffin vesicles contained $A\beta_{1-40}$ at 0.051 pg/ug protein as determined by RIA and a detectable amount of $A\beta_{1-42}$ as determined by ELISA.

The above-identified references are expressly incorporated herein. Although the invention has been described with reference to the examples provided above, it should be understood that various modifications can be made without departing from the spirit of the invention. Accordingly, the invention is limited only by the claims.

I claim:

1. A method of selecting an agent that alters the cleavage of an amyloid precursor protein (APP) substrate by a secretase, comprising the steps of:
   a) obtaining substantially pure vesicles;
   b) permeabilizing the substantially pure vesicles;
   c) incubating the permeabilized vesicles with the APP substrate in a first incubation solution;
   d) detecting the cleavage of the APP substrate in the first incubation solution, wherein the amount of cleavage is proportional to the proteolytic activity of the secretase;
   e) incubating the agent, the permeabilized vesicles, and the APP substrate in a second incubation solution;
   f) detecting the cleavage of the APP substrate in second incubation solution, wherein the amount of cleavage is proportional to the proteolytic activity of the secretase;
   g) comparing the cleavage of the APP substrate in the first and second incubation solutions; and
   h) the agent is thereby selected that alters the cleavage of the APP substrate of the second incubation solution from that in the first incubation solution.

2. The method of claim 1, wherein the secretase is selected from the group consisting of β-secretase, γ-secretase, and α-secretase.

3. The method of claim 1, wherein the vesicles are secretory vesicles.

4. The method of claim 1, wherein the vesicles are chromaffin vesicles.

5. A method of selecting an agent that alters the cleavage of an amyloid precursor protein (APP) substrate by a secretase, comprising the steps of first isolating the secretase by:
   a) obtaining substantially pure vesicles;
   b) permeabilizing the substantially pure vesicles;
   c) incubating the permeabilized vesicles with the APP substrate;
   d) detecting the cleavage of the APP substrate in the first incubation solution, wherein the amount of cleavage is proportional to the proteolytic activity of the secretase; and
   e) thereby isolating the secretase having the activity;
and then selecting the agent by:
   f) incubating the secretase that is isolated with the APP substrate in a first incubation solution;
   g) detecting the cleavage of the APP substrate in the second incubation solution, wherein the amount of cleavage is proportional to the proteolytic activity of the secretase that is isolated;
   h) incubating the secretase that is isolated, the APP substrate and the agent in a second incubation solution;
   i) determining the cleavage of the APP substrate in the second incubation solution, wherein the amount of cleavage is proportional to the proteolytic activity of the secretase that is isolated;
   j) comparing the cleavage of the APP substrate in the first and second incubation solutions; and k) the agent is thereby selected that alters the cleavage of the APP substrate of the second incubation solution from that in the first incubation solution.

6. The method of claim 5, wherein the secretase is selected from the group consisting of β-secretase, γ-secretase, and α-secretase.

7. The method of claim 5, wherein the vesicles are secretory vesicles.

8. The method of claim 5, wherein the vesicles are chromaffin vesicles.

* * * * *